US009283738B2

(12) United States Patent
Miyachika et al.

(10) Patent No.: US 9,283,738 B2
(45) Date of Patent: Mar. 15, 2016

(54) METHOD FOR PRODUCING PRESSURE-SENSITIVE ADHESIVE TAPE PACKAGE

(71) Applicant: HISAMITSU PHARMACEUTICAL CO., INC., Tosu-shi, Saga (JP)

(72) Inventors: Takafumi Miyachika, Tosu (JP); Kiyotaka Takada, Tosu (JP)

(73) Assignee: Hisamitsu Pharmaceutical Co., Inc., Saga (JP)

( * ) Notice: Subject to any disclaimer, the term of this patent is extended or adjusted under 35 U.S.C. 154(b) by 11 days.

(21) Appl. No.: 14/353,107

(22) PCT Filed: Oct. 23, 2012

(86) PCT No.: PCT/JP2012/077321
§ 371 (c)(1),
(2) Date: Apr. 21, 2014

(87) PCT Pub. No.: WO2013/061951
PCT Pub. Date: May 2, 2013

(65) Prior Publication Data
US 2014/0246144 A1    Sep. 4, 2014

(30) Foreign Application Priority Data
Oct. 24, 2011   (JP) ................................ P2011-233069

(51) Int. Cl.
*A61F 13/02*   (2006.01)
*B32B 37/26*   (2006.01)
(Continued)

(52) U.S. Cl.
CPC ............. *B32B 37/26* (2013.01); *A61F 13/0008* (2013.01); *A61F 13/0276* (2013.01);
(Continued)

(58) Field of Classification Search
None
See application file for complete search history.

(56) References Cited

U.S. PATENT DOCUMENTS 2,698,046 A * 12/1954 Finke .......................... 156/200
4,264,008 A    4/1981 Kozlow
(Continued)

FOREIGN PATENT DOCUMENTS

EP    0848937 A2    6/1998
EP    2377498 A1    10/2011
(Continued)

OTHER PUBLICATIONS

PCT/JP2012/077321, International Preliminary Report on Patentability, May 8, 2014, Ten (10) pages.
(Continued)

*Primary Examiner* — Barbara J Musser
(74) *Attorney, Agent, or Firm* — Nath, Goldberg & Meyer; Joshua B. Goldberg; Tanya E. Harkins

(57) ABSTRACT

An object of the present invention is to provide a method for producing a pressure-sensitive adhesive tape package suitable for mass production. The production method according to the present invention aims at producing a pressure-sensitive adhesive tape package which is a pressure-sensitive adhesive tape package 10 accommodating a pressure-sensitive adhesive tape 14 having a support 18 and an adhesive agent layer 12 provided on one surface of the support 18, the pressure-sensitive adhesive tape package comprising a release sheet 16 to which the adhesive agent layer of the adhesive tape is releasably attached. In this method, the adhesive tape 14 is bonded to the release sheet base material 116, and folded in two. Subsequently, a plurality of adhesive tapes 14 is heat sealed and temporarily attached to one release sheet base material 116, and the release sheet base material 116 is cut.

12 Claims, 16 Drawing Sheets

(51) Int. Cl.
  *B32B 38/00* (2006.01)
  *A61F 13/00* (2006.01)
  *C09J 7/02* (2006.01)

(52) U.S. Cl.
  CPC ......... *A61F13/0279* (2013.01); *B32B 38/0004* (2013.01); *C09J 7/0207* (2013.01); *B32B 2037/268* (2013.01); *Y10T 156/1015* (2015.01); *Y10T 156/1036* (2015.01)

(56) References Cited

U.S. PATENT DOCUMENTS

| | | | | |
|---|---|---|---|---|
| 6,475,325 | B1* | 11/2002 | Parrish et al. | 156/265 |
| 2008/0202675 | A1* | 8/2008 | Sever et al. | 156/238 |

FOREIGN PATENT DOCUMENTS

| | | |
|---|---|---|
| GB | 1029560 | 5/1966 |
| JP | S48-094190 | 11/1973 |
| JP | 61-151288 | 7/1986 |
| JP | 11-060474 | 3/1999 |
| JP | 2004-344328 | 12/2004 |
| JP | 2006-306419 | 11/2006 |
| WO | 94/21207 | 9/1994 |
| WO | 2010/071104 A1 | 6/2010 |

OTHER PUBLICATIONS

Search Report issued in International Application No. PCT/JP2012/077321 dated Jan. 29, 2013, two (2) pages.
Singapore Patent Application No. 11201401668U, Office Action dated Apr. 6, 2015, ten (10) pages.
European Patent Application No. 12843256.4, Extended European Search Report dated Aug. 4, 2015, five (5) pages.

\* cited by examiner

Fig.2
(a)
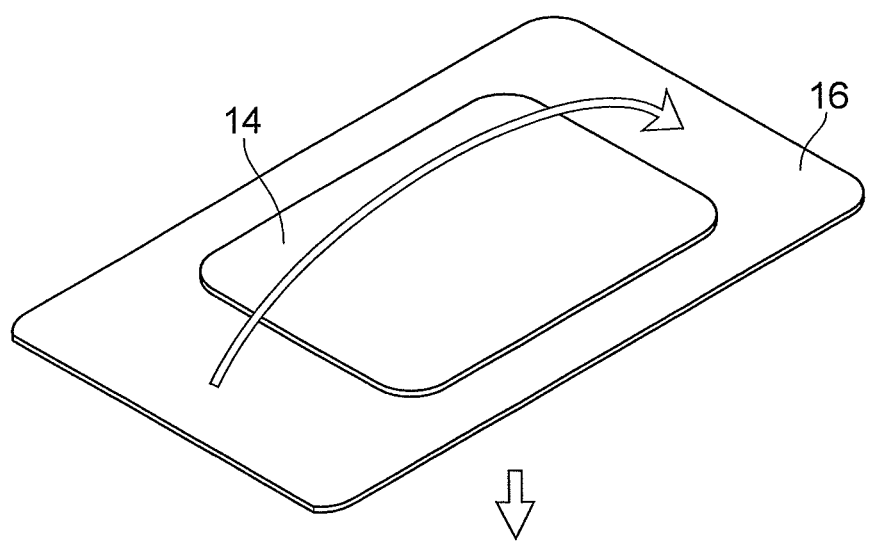
(b)
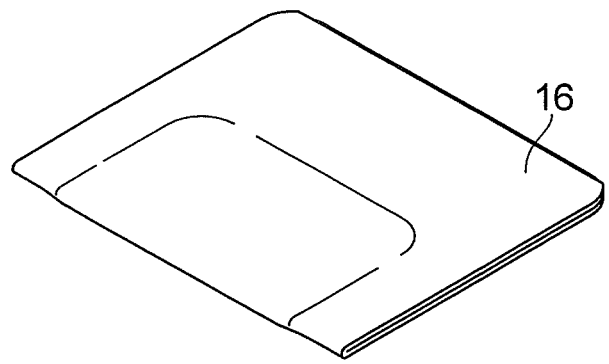
(c)
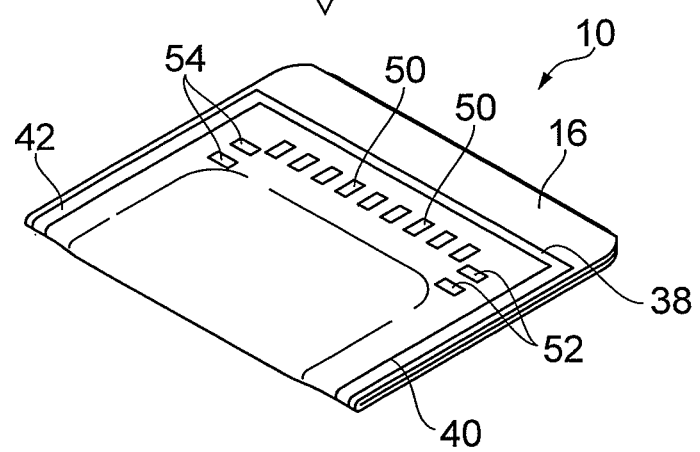

*Fig.4*
(a)
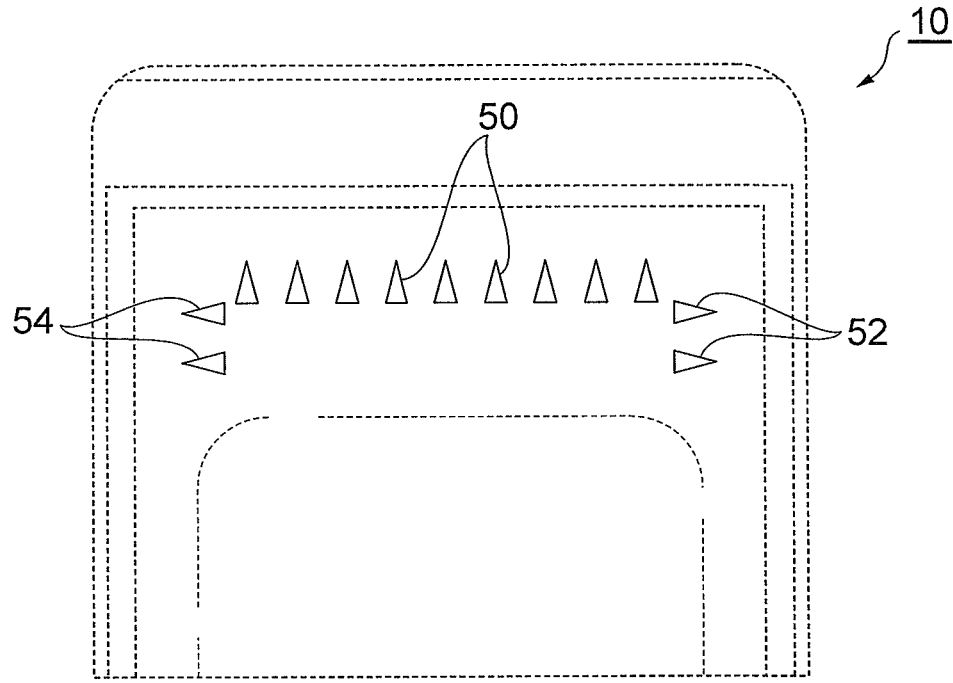
(b)
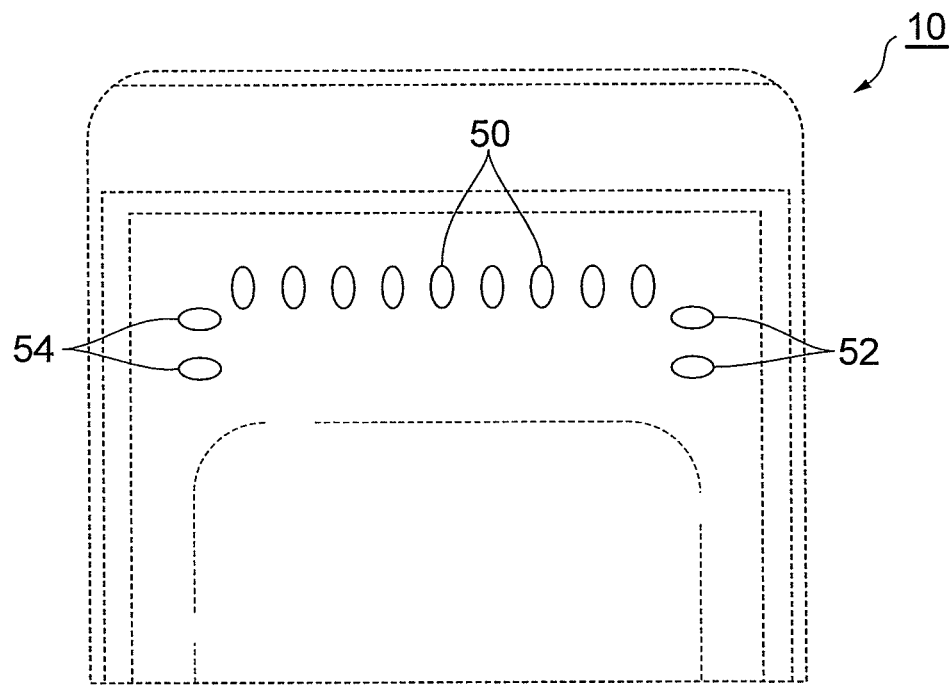

Fig.5
(a)
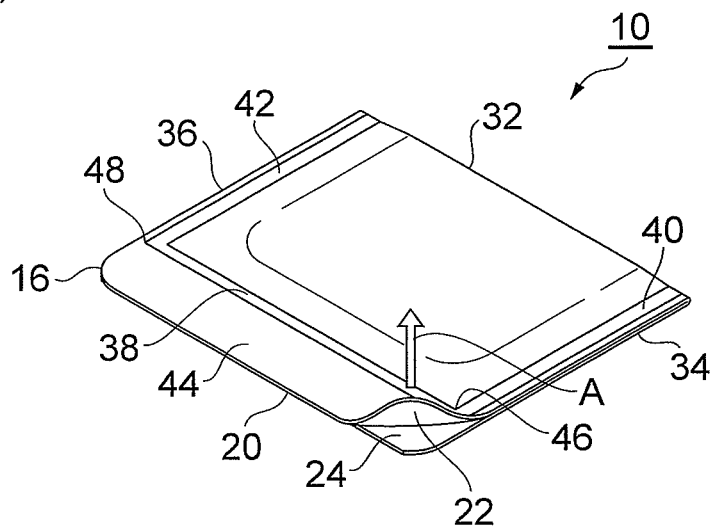
(b)
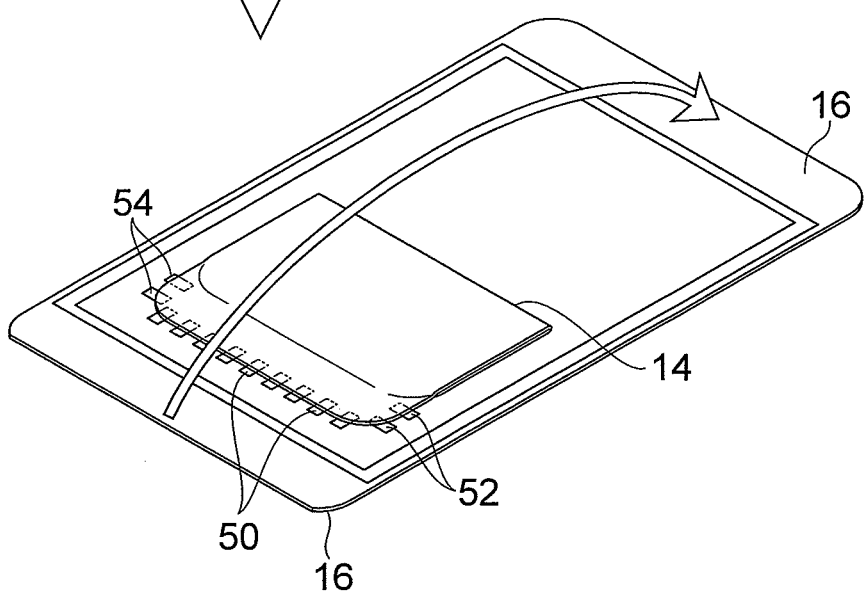

METHOD FOR PRODUCING PRESSURE-SENSITIVE ADHESIVE TAPE PACKAGE

This is a National Phase Application filed under 35 U.S.C. §371 as a national stage of PCT/JP2012/077321, filed on Oct. 23, 2012, an application claiming the benefit under 35 U.S.C. §119 of Japanese Application No. P2011-233069, filed on Oct. 24, 2011, the content of each of which is hereby incorporated by reference in their entirety.

TECHNICAL FIELD

The present invention relates to a package that packs a pressure-sensitive adhesive tape having an adhesive agent layer on a support, and more specifically relates to a method for producing the package.

BACKGROUND ART

Pressure-sensitive adhesive tapes in a variety of forms have conventionally been known and used for labels, medical care, cosmetics, decoration, masking, industries, and other various applications. The adhesive tape used for medical care is in a form of a patch preparation such as a poultice, a plaster, an adhesive bandage, a surgical tape, and a tape preparation, and usually applied onto a skin, a mucous membrane, or the like.

Such an adhesive tape usually comprises a support and an adhesive agent layer provided on one surface of the support, and a release sheet releasably attached to the adhesive agent layer. The adhesive tape, after production, may be cut into an appropriate size and distributed and sold in the state of being individually contained in a package for hygienic and physical protection. In this case, at the time of use thereof, the adhesive agent layer is applied onto a portion for application after tearing the package to remove the adhesive tape therefrom, and release the release sheet to expose the adhesive agent layer.

A problem that occurs at the time of use in some cases is difficulties in releasing the release sheet. That is, because the release sheet is usually thin and soft, it is difficult to handle, and it may take some time to release the release sheet. At the time of use of the adhesive tape, the release sheet and the package are turned into a waste after use.

Then, a pressure-sensitive adhesive tape package described in Patent Literature 1 has been proposed in the related art. The package is a package in which an adhesive tape is bent into two such that an adhesive agent layer faces outwardly, the two-folded adhesive tape is covered with a release sheet so as to sandwich the adhesive tape inside of the release sheet, and the periphery of the release sheet is sealed. In this configuration, the release sheet functions as a package, and thus the package needed in the related art can be eliminated.

Moreover, to expose only a half of the adhesive agent layer when the front portion of the release sheet is pulled off from the rear portion thereof to open the package, means for temporarily attaching the half located on the front side of the two-folded adhesive tape to the rear portion of the release sheet is provided. Thereby, application to a portion for application is easy because when the package is opened, the adhesive tape folded in two is held by the front portion of the release sheet and the half on the front side of the adhesive agent layer is exposed.

CITATION LIST

Patent Literature

Patent Literature 1: WO2010/071104

SUMMARY OF INVENTION

Technical Problem

It is easy to produce the above pressure-sensitive adhesive tape package one by one, but various devices are needed in mass production. Accordingly, an object of the present invention is to provide a method for producing a pressure-sensitive adhesive tape package suitable for mass production.

Solution to Problem

In order to achieve the above object, the method for producing a pressure-sensitive adhesive tape package according to the present invention is a method for producing a pressure-sensitive adhesive tape package, the pressure-sensitive adhesive tape package accommodating a pressure-sensitive adhesive tape having a support and an adhesive agent layer provided on one surface of the support, the pressure-sensitive adhesive tape package comprising a release sheet to which the adhesive agent layer of the adhesive tape is releasably attached, the method comprising: a step of feeding a release sheet base material serving as the release sheet to a predetermined feed position; a step of sequentially feeding a plurality of adhesive tapes in a row to the release sheet base material at the feed position, and boding the adhesive tapes to the release sheet base material such that predetermined spaces are formed between the adhesive tapes adjacent in anterior and posterior directions of the feeding direction; a step of folding the release sheet base material with the adhesive tape in two; a step of sealing a predetermined portion of the release sheet base material to form the two-folded release sheet base material including a plurality of accommodating spaces each of which accommodates one adhesive tape; a step of temporarily attaching a part of each adhesive tape to the release sheet base material; and a step of cutting the release sheet base material to form pressure-sensitive adhesive tape packages.

As the step of bonding the adhesive tapes to the release sheet base material, a step comprising a substep of cutting an adhesive tape base material serving as the adhesive tape to form a row of adhesive tapes and a substep of separating adjacent adhesive tapes from each other, and conveying the adhesive tapes to the feed position with an interval between the adjacent adhesive tapes being increased is thought.

Alternatively, the step of boding the adhesive tapes to the release sheet base material may comprises a substep of half-cutting an adhesive tape base material having a liner without cutting the liner so as to form a row of adhesive tapes on the liner, and a substep of conveying the adhesive tapes to the feed position while the liner is being released.

In the above method, the adhesive tapes in a row are fed to the release sheet base material. It is also thought that the adhesive tapes are formed in two or more rows, and the interval between the adhesive tapes is increased not only anterior and posterior directions to the feeding direction but also in the left and right traverse directions thereof. In this case, a plurality of rows of a plurality of adhesive tapes are sequentially fed to the release sheet base material at the feed position, and the adhesive tapes are bonded to the release sheet base material such that predetermined spaces are formed between adjacent adhesive tapes in anterior, posterior, left, and right directions of the feeding direction. The release sheet base material is then slit along the longitudinal direction thereof to form a plurality of release sheet base materials, a row of adhesive tapes being bonded to each of the release sheet base materials.

The step of bonding the adhesive tapes to the release sheet base material comprises a substep of cutting an adhesive tape web into a plurality of rows of adhesive tapes and a substep of separating adhesive tapes adjacent in anterior, posterior, left, and right directions from each other and conveying the adhesive tapes to the feed position with the intervals therebetween being increased.

Alternatively, the step of bonding the adhesive tapes to the release sheet base material may comprise a substep of half-cutting an adhesive tape base material having a liner without cutting the liner so as to form a plurality of rows of adhesive tapes on the liner, and a substep of conveying the adhesive tapes to the feed position while the liner is being released.

It is preferable that the sealing is heat sealing. It is preferable that temporary attachment is performed by thermal bonding.

Furthermore, it is preferable that in the step of sealing a predetermined portion of the release sheet base material, two sealed portions are formed at a constant interval between adjacent accommodating spaces, and in the step of cutting the release sheet base material, cutting is performed between the two sealed portions.

Advantageous Effects of Invention

According to the production method according to the present invention, production efficiency is improved because the adhesive tapes are bonded to the release sheet base material, and the release sheet base material is folded in two, and is cut. Namely, if the release sheet base material is cut in advance to prepare release sheets having a size of the product, and the adhesive tapes are bonded to the release sheets one by one, a complex production facility for handling separated release sheets and separated adhesive tapes is needed, leading to poor efficiency and an increase in cost of the production facility. The method according to the present invention has no such problems, and improves production efficiency remarkably.

Moreover, after the adhesive tapes are bonded to the release sheet base material, a plurality of adhesive tapes can be accommodated in a single release sheet base material in batch and be temporarily attached to the release sheet base material. This also contributes to improvement in production efficiency.

BRIEF DESCRIPTION OF DRAWINGS

FIGS. 2(a) to 2(c) are perspective views showing a simple method for producing the pressure-sensitive adhesive tape package in FIG. 1.

FIGS. 4(a) and 4(b) are drawings showing other shapes of the temporary attach portion, respectively.

FIGS. 5(a) and 5(b) are perspective views showing a method for using the pressure-sensitive adhesive tape package in FIG. 1.

FIG. 8(a) is a plan view thereof, and FIG. 8(b) is a side view thereof.

DESCRIPTION OF EMBODIMENTS

Figure 1:
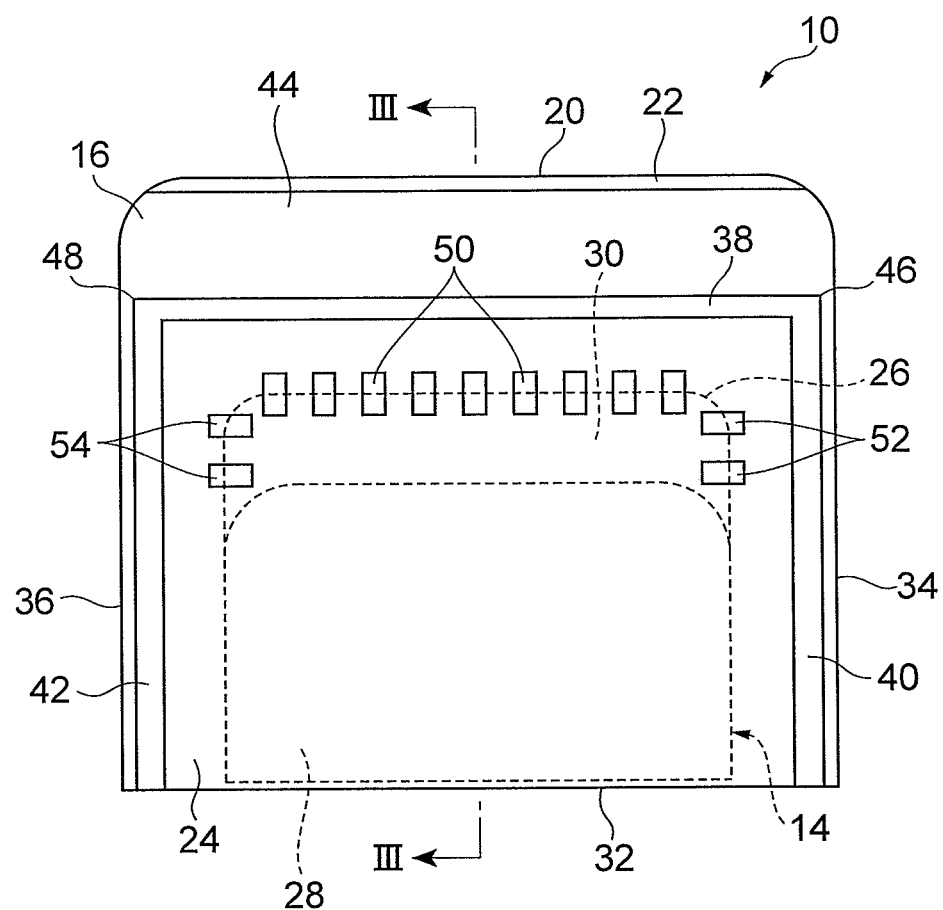
FIG. 1 is a front view of a pressure-sensitive adhesive tape package produced by a method for producing a pressure-sensitive adhesive tape package according to the present invention.

Hereinafter, with reference to the drawings, suitable embodiments according to the present invention will be described. Through all the drawings, same reference numerals will be given to same or equivalent portions, and the duplicate description thereof will be omitted.

Figure 3:
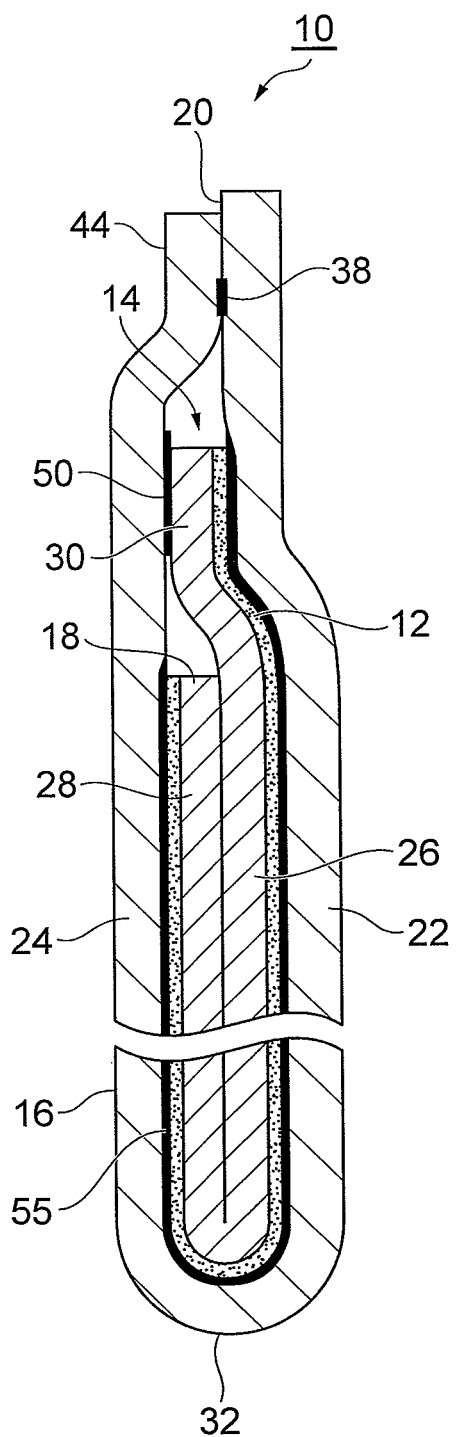
FIG. 3 is a schematic sectional view taken along the line in FIG. 1.

FIG. 1 is a front view showing a pressure-sensitive adhesive tape package 10 which can be produced by a production method according to the present invention, and FIGS. 2(a) to 2(c) are perspective views showing a configuration of the pressure-sensitive adhesive tape package 10 in FIG. 1 in more detail. FIG. 3 is a schematic sectional view taken along the line in FIG. 1.

The shown pressure-sensitive adhesive tape package 10 includes a pressure-sensitive adhesive tape 14 having an adhesive agent layer 12 on one surface thereof, and a release sheet 16 for sealing the adhesive tape 14 folded in two. The adhesive tape 14 and the release sheet 16 both are rectangular. As understood from FIG. 1 and FIG. 2(c), the pressure-sensitive adhesive tape package 10 is the so-called three-sealed package type in which one release sheet 16 is bent, and three sides except the bend side are sealed.

The pressure-sensitive adhesive tape package 10 is used for labels, medical care, cosmetics, decoration, masking, industries, and other various applications. Particularly, the pressure-sensitive adhesive tape package used for medical care, cosmetics, and the like can be used as a package of a patch preparation such as a plaster, a poultice, an adhesive bandage, a surgical tape, a cosmetic face pack preparation, a tape preparation, and an adhesive heating pack that is usually applied to a skin, a mucous membrane, and the like.

As shown in FIG. 3, the adhesive tape 14 includes a support 18, and the adhesive agent layer 12 laminated on the one surface thereof, and the release sheet 16 is releasably attached to this. The component material of the support 18 is not limited as long as it can support the adhesive agent layer 12, and usually, woven fabrics, non-woven fabrics, films made of a plastic or the like, metallic foils, and the like are used. Further, the support may be a single layer structure or a laminate structure; it may be a structure in which a plurality of woven fabrics or non-woven fabrics made of different materials is laminated, or a structure in which a plastic film, a metallic foil, or the like and a woven fabric or a non-woven fabric are laminated, for example.

Moreover, the woven fabric or non-woven fabric used for the adhesive tape 14 of the present embodiment is not particularly limited, and may be those obtained by processing a fibrous material into a fabric and applicable for the support 18 of the adhesive tape 14; examples thereof include a knitted fabric processed into a fabric by collecting stitches by circular knit, warp knit, weft knit, and the like.

Preferable examples of the woven fabric or non-woven fabric include woven fabrics or non-woven fabrics made of at least one kind of resin fibers selected from the group consisting of polyester resins, polyethylene resins, and polypropylene resins; among them, the woven fabrics made of polyethylene terephthalate that is polyester with less interaction with the component contained in the adhesive agent layer are preferable.

Examples of the plastic film include those formed using polyesters such as polyethylene terephthalate, polyamides such as nylon, polyolefins such as polyethylene and polypropylene, polyvinyl chloride, plasticized polyvinyl chloride, plasticized vinyl acetate-vinyl chloride copolymers, polyvinylidene chloride, ethylene-vinyl acetate copolymers, cellulose acetate, ethyl cellulose, ethylene-ethyl acrylate copolymers, polytetrafluoroethylene, polyurethanes, and ionomer resins. Moreover, in the case where the adhesive tape 14 is used as the patch preparation for medical care or cosmetics, it is preferable that a material having sufficient stretchability or non-stretchability as a patch preparation is used for the support 18, and a polyethylene terephthalate hosiery woven fabric (knitted fabric) is particularly preferable.

It is preferable that in the knitted fabric as the support 18, the basis weight (mass per units) is 50 to 500 g/m$^2$. Moreover, in the case where the support 18 is measured according to the method of JIS L1018, it is preferable that the modulus in the longitudinal length (long axis direction) is 2 to 12 N/5 cm, and the modulus in the traverse direction (short axis direction) is also 2 to 12 N/5 cm. The longitudinal length here refers to a flow direction at a step of producing a knitted fabric, and the traverse direction refers to a direction perpendicular to the longitudinal length, namely the width direction. In the case where the modulus is smaller than 2 N/5 cm in the longitudinal length or traverse direction, application to the portion for application while unwrinkling tends to be difficult; moreover, in the case where the modulus is larger than 12 N/5 cm in the longitudinal length or traverse direction, conversely, the adhesive tape tends to be excessively stretched during application to cause wrinkles. The modulus is a value of the stress at room temperature (25° C.), and at 50% extension.

By use of the support 18 above, temporary attach portions 50, 52, and 54 by the temporary attaching means described later is facilitated, and the shape and structure of the support 18 after the support is removed from the temporary attach portions 50, 52, and 54 are hardly changed. Namely, fuzzing or the like is not produced, for example. Moreover, bending the pressure-sensitive adhesive tape package 10 into two is easy, and the bent pressure-sensitive adhesive tape package is not bulky. Further, the so-called "kink" is hardly produced in the portion that is bent into two during application, and the adhesive tape is applied neatly.

The adhesive component that is the component material of the adhesive agent layer 12 is not particularly limited as long as it has adhesiveness and can be applied to the portion for application; acrylic adhesive components, rubber based adhesive components, silicone based adhesive components, and the like are preferably used as an adhesive base; among them, the rubber based adhesive components are particularly preferably used from the viewpoint of adhesiveness.

As a specific example of the rubber based adhesive component, natural rubbers and synthetic rubbers both can be used, and examples of the synthetic rubbers include styrene block copolymers and polyisobutylene. Further, examples of the styrene block copolymers include styrene-butylene-styrene block copolymers (SBS), styrene-isoprene-styrene block copolymers (SIS), styrene-ethylene/butylene-styrene block copolymers (SEBS), and styrene-ethylene/propylene-styrene block copolymers (SEPS). Specific examples of the styrene block copolymers include linear triblock copolymers such as Kraton D-1112, D-1111, and D-1107 (trade name, made by Kraton Performance Polymers Inc), JSR5000 or JSR5002 (trade name, made by JSR Corporation), Quintac 3530, 3421 or 3570C (trade name, made by Zeon Corporation), and Kraton D-KX401CS or D-1107CU (trade name, made by Kraton Performance Polymers Inc), and branched block copolymers such as Kraton D-1124 (trade name, made by Kraton Performance Polymers, Inc.) and Solprene 418 (trade name, made by Phillips Petroleum Company).

As polyisobutylene, for example, high or low molecular weight are used, and examples thereof include Oppanol B10, B12, B12SF, B15, B15SF, B30SF, B50, B50SF, B80, B100, B120, B150, and B200 (trade name, made by BASF SE), and Vistanex LM-MS, LM-MH, LM-H, MM L-80, MM L-100, MM L-120, and MM L-140 (trade name, made by Exxon Chemical Company).

Moreover, as the acrylic polymer, a polymer or copolymer containing at least one (meth)acrylate ester such as 2-ethylhexyl acrylate, methyl acrylate, butyl acrylate, hydroxyethyl acrylate, 2-ethylhexyl-methacrylate as a monomer unit is used, and acrylic acid/acrylic acid octyl ester copolymers, 2-ethylhexyl acrylate/N-vinyl-2-pyrrolidone/1,6-hexaneglycol dimethacrylate copolymers, 2-ethylhexyl acrylate/vinyl acetate copolymers, 2-ethylhexyl acrylate/vinyl acetate/acrylic acid copolymers, 2-ethylhexyl acrylate/2-ethylhexyl-methacrylate/dodecyl methacrylate copolymers, a methyl acrylate/2-ethylhexyl acrylate co polymerized resin emulsion, an adhesive agent of an acrylic polymer or the like contained in an acrylic resin alkanolamine solution, DUROTAK acrylic adhesive agent series (made by National Starch and Chemical Company), GELVA acrylic adhesive agent series (made by Monsanto Company), SK-Dyne Matriderm (Soken Chemical & Engineering Co., Ltd.), EUDRAGIT series (Higuchi Inc.), and the like can be used, for example.

One of the adhesive bases such as the rubber adhesive base, the acrylic adhesive base, and the silicone adhesive base above can be used, or two or more thereof can be mixed and used.

Further, in the case where the adhesive tape 14 is used as a poultice or a plaster for medical care or a cosmetic face pack agent, a water-soluble polymer can also be used as the adhesive agent layer 12; as such a water-soluble polymer, gelatin, agar, alginic acid, mannan, carboxymethyl cellulose or salts thereof, hydroxypropyl cellulose or salts thereof, polyvinyl alcohol, polyacrylic acid or salts thereof, and the like, or those obtained by crosslinking at least one of these by an organic or inorganic crosslinking agent are preferably used.

Other than the adhesive bases above, a tackifier, a softening agent, a solvent, water, a thickener, a wetting agent, a filler, a crosslinking agent, a polymerizing agent, a solubilizing agent, an absorption promoter, a stabilizer, an antioxidant, an emulsifier, a surface active agent, a pH adjuster, drugs, an ultraviolet absorbing agent, and the like are properly added to the adhesive agent layer.

The drugs in the case where the adhesive tape 14 is used as the patch preparation for medical care and cosmetics are not particularly limited as long as they are percutaneously absorbed into the body to demonstrate a pharmacological effect, and examples thereof include an antiinflammatory agent, an analgesic agent, an antihistamine, a local anesthetic agent, a blood circulation promoter, an anesthetic agent, a tranquilizer, an antihypertensive agent, an antibacterial agent, and a vasodilator.

The release sheet 16 usually used for the package of the adhesive tape 14 can be used. The release sheet 16 may be formed of a single layer or a laminate, and the constitutional material is not particularly limited as long as the innermost layer (layer which is the inside of the package) can be used in the production method according to the present invention, and particularly, can be heat sealed or thermally bonded. For example, the base material of the release sheet 16 can be properly selected from paper, non-woven fabrics, aluminum, cellophane, nylon, high density or low density polyethylene, polyethylene terephthalate, polypropylene, polyvinyl chloride, polyamide, polyvinylidene chloride, polyvinyl alcohol, polyvinyl acetate copolymers, polycarbonate, polystyrene, ethylene vinyl alcohol copolymers, and the like. Among these, when a material that cannot be molten by heating is used as the base material, a laminate of a thermoplastic material is suitable for the layer that is the inside of the package. Particularly, a sheet made of polyethylene, aluminum, and polyethylene sequentially stacked is preferable, and a sheet thereof further including the outermost layer (layer that is the outside of the package) of cellophane is preferably used.

Further, the release sheet may be those in which a printing ink or an adhesive is applied to the outermost layer, or those on which a thin film is provided by a method such as deposition or sputtering. As the thin film, thin films with high gas barrier properties and transparency made of silicon oxide, magnesium oxide, and aluminum oxide other than metals such as aluminum are suitable.

Because these release sheets 16 are bent when the adhesive tape 14 is sealed, those having flexibility are preferable. Accordingly, the thickness of the release sheet 16 is not particularly limited as long as it can be bent, and it is preferable that the thickness is in the range of 10 to 500 μm, and it is more preferable that the thickness is in the range of 15 to 300 μm.

Here, with reference to FIG. 2(a), FIG. 2(a) shows the state in which the adhesive tape 14 is releasably attached onto the release sheet 16 with the adhesive agent layer 12 facing downwardly. In this state, the adhesive tape 14 is attached to the release sheet 16 in a state where the center line parallel to the short direction of the adhesive tape 14 may be displaced from the center line parallel to the short direction of the release sheet 16. When the release sheet 16 and the adhesive tape 14 are bent together, as shown in (b) of FIG. 2, the adhesive tape 14 folded in two is sandwiched in the two-folded release sheet 16.

Here, assume that a half of the bent release sheet 16 is referred to as the first portion 22, the other half thereof is referred to as the second portion 24, a half of the adhesive tape 14 bent with the release sheet 16 is referred to as a first portion 26, and the other half thereof is referred to as a second portion 28. With the release sheet 16 bent, the first portion 22 and the second portion 24 of the release sheet 16 have substantially the same shape and size, while the adhesive tape 14 is in the state where the first portion 26 is larger than the second portion 28 and the first portion 26 has an extending portion 30 extending from the second portion 28. In this state, of the portion of the release sheet 16 in which the first portion 22 is layered on the second portion 24, the three sides surrounding the adhesive tape 14 are heat sealed to obtain the pressure-sensitive adhesive tape package 10 shown in FIGS. 1, 2(c), and 3.

In such a pressure-sensitive adhesive tape package 10, when the first portion 22 of the release sheet 16 is pulled off from the second portion 24 thereof to open the package, the adhesive agent layer 12 in the two-folded adhesive tape 14 faces outwardly. Accordingly, the adhesive agent layer 12 in the first portion 26 in the adhesive tape 14 is exposed to the outside.

However, if the first portion 26 of the adhesive tape 14 moves together with the first portion 22 of the release sheet 16 and the adhesive agent layer 12 in the second portion 28 of the adhesive tape 14 is exposed, whether the adhesive agent layer 12 is exposed on the front side or rear side cannot be known, and this is inconvenient. Namely, it is important to primarily hold the first portion 26 of the adhesive tape 14 by the second portion 24 of the release sheet 16 when the package is opened, and expose the adhesive agent layer 12 in the first portion 26 of the adhesive tape 14. Then, the extending portion 30 formed on the first portion 26 of the adhesive tape 14 is temporarily attached to the second portion 24 of the release sheet 16 at places indicated by symbols 50, 52, and 54.

Thermal bonding is effective as the temporary attach means. Namely, when heat is applied from the outer surface side of the release sheet 16, the thermoplastic material that forms the innermost layer of the release sheet 16 is molten, adheres to the support 18 in the adhesive tape 14, and is then solidified. For this reason, the extending portion 30 of the adhesive tape 14 is temporarily attached to the second portion 24 of the release sheet 16. Particularly, when the support 18 of the adhesive tape 14 is made of a woven fabric or a knitted fabric, a molten thermoplastic material permeates into the support, and the temporary attaching effect is further improved.

Moreover, for the position in which the temporary attach portions 50, 52, and 54 is disposed, as shown in FIG. 1, it is suitable that the temporary attach portions 52, 54 is formed on not only the line along the first sealed portion 38 but also the line along the second sealed portion 40 and the line along the third sealed portion 42. Thereby, even if the first portion 22 of the release sheet 16 is pulled off from the second portion 24 thereof in the traverse direction, the temporary attaching effect can be guaranteed. The lines on which the temporary attach portions 50, 52, and 54 are disposed are not limited to straight lines. The lines may be curves, or may be disposed on multiplets. Furthermore, it can be thought that the lines are disposed in a staggered pattern, a zigzag pattern, or a random patter as long as the lines are aligned with the first sealed portion 38, the second sealed portion 40, and the third sealed portion 42, respectively.

If the adhesive force is excessively increased by the temporary attach portions 50, 52, and 54, a problem that the adhesive tape 14 is difficult to release from the release sheet 16 in application to the portion for application may arise. Then, the adhesive force of the extending portion 30 of the adhesive tape 14 to the release sheet 16 is preferably larger than the adhesive force (tackiness) of the adhesive agent layer 12 to the release sheet 16. Namely, the adhesive force of the support 18 to the release sheet 16 through the temporary attach portions 50, 52, and 54, the adhesive force (tackiness) of the adhesive agent layer 12 of the adhesive tape 14 to the portion for application, and the adhesive force of the adhesive agent layer 12 of the adhesive tape 14 to the release sheet 16 are in a relation as follows.

the adhesive force of the adhesive agent layer 12 to the portion for application
the adhesive force of the support 18 to the release sheet 16 through the temporary attach portions 50, 52, and 54
the adhesive force of the adhesive agent layer 12 to the release sheet 16

In the case where the temporary attach portions 50, 52, and 54 is in a continuous band-like shape, it can be thought that the amount of the thermoplastic material in the release sheet 16 to be impregnated into the woven fabric of the support 18 in the adhesive tape 14 is excessively large, and it is difficult to obtain the relationship above. Then, in the present invention, as shown in FIGS. 1 to 3 by symbols 50, 52, and 54, the temporary attach portions 50, 52, and 54 is discontinuously formed to adjust the number and size of temporary attach portions 50, 52, and 54. Thereby, the adhesive force of the temporary attach portions 50, 52, and 54 can be easily adjusted. Thereby, the production efficiency of the pressure-sensitive adhesive tape package 10 is further improved, and constant quality can be ensured in the action effect. Note that the shapes of the temporary attach portions 50, 52, and 54 are also not limited to the rectangular shape shown in FIG. 1, and various shapes such as a triangular shape shown in FIG. 4(a) and an oval shape shown in FIG. 4(b) can be thought.

Further, it is preferable that the release sheet 16 has means for reducing an adhesive force 55 that reduces an adhesive force between the adhesive agent layer 12 of the adhesive tape 14 and the release sheet 16. As this means for reducing an adhesive force 55, the innermost layer of the release sheet 16 may be subjected to the releasing treatment. Examples of the releasing treatment include, other than a method using a release agent, a method such as embossing and sandmat processing that physically makes releasing easy. As the release agent, any of silicone release agents, alkyl pendant release agents, condensed wax release agents, and the like can be used; among these, the silicone treatment using the silicone release agent is preferable. The silicone treatment is advantageous in that it is performed relatively easily and at low cost. By performing the silicone treatment, in corporation with said the temporary attach portions 50, 52, and 54, upon use of the pressure-sensitive adhesive tape package 10, when the release sheet 16 is opened, the adhesive agent layer 12 is easily removed from the release sheet 16 to expose the adhesive agent layer 12; for this reason, application to the portion for application is easy. As described above, the means for reducing an adhesive force 55 may be provided across the adhesive agent layer 12 of the adhesive tape 14, or may be provided to cover only the adhesive agent layer 12 in the first portion 26 of the adhesive tape.

Figure 6:
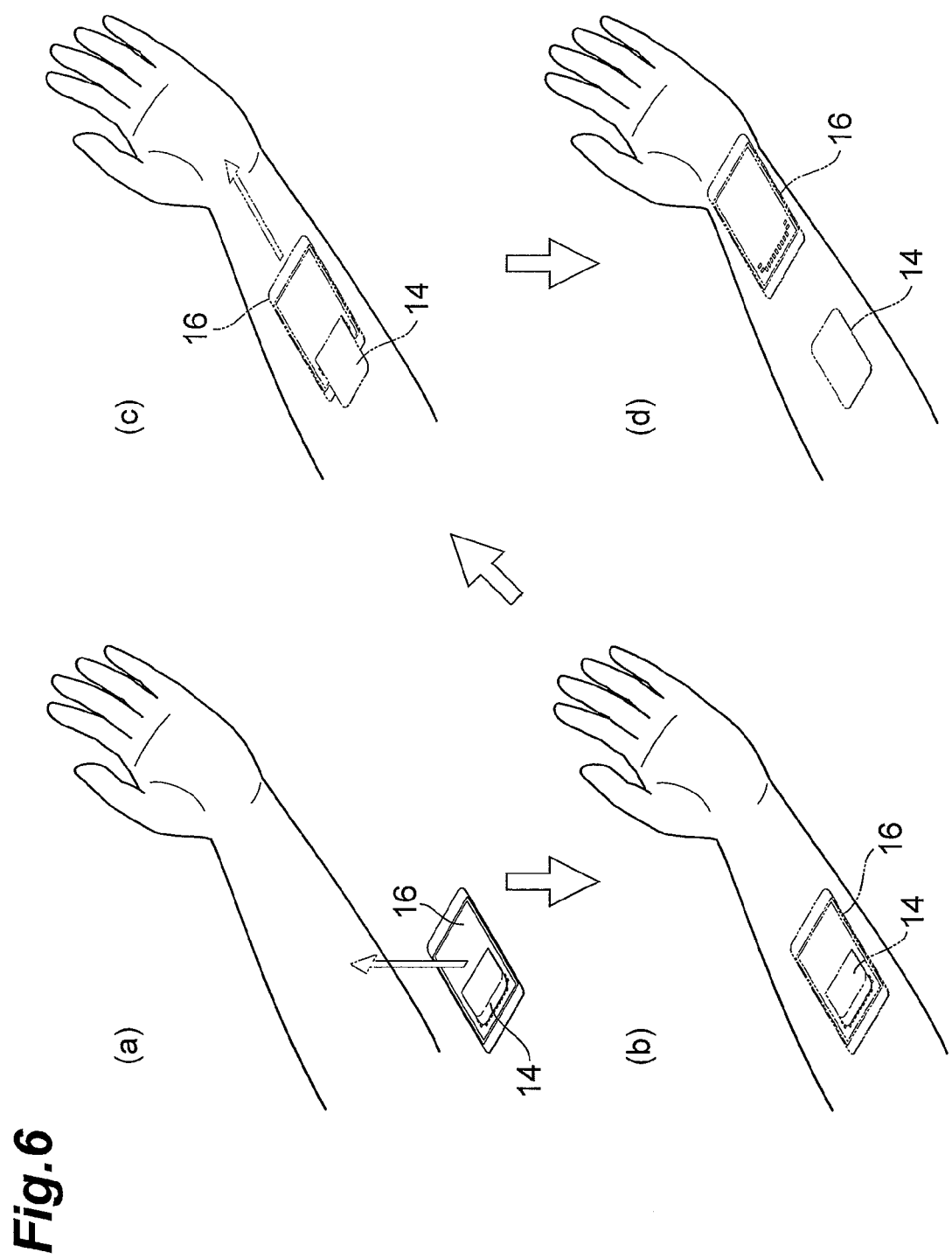
FIGS. 6(a) to 6(d) are drawings illustrating scenes in which an adhesive tape is applied to a portion for application using the pressure-sensitive adhesive tape package in FIG. 1.

Next, with reference to FIGS. 5 and 6, the action of the pressure-sensitive adhesive tape package 10 according to the present embodiment will be described.

FIG. 5(a) shows a perspective view of the pressure-sensitive adhesive tape package 10 according to the present embodiment. From this state, a user holds the holding portion 44 of the release sheet 16 (fingers are not shown), and starts to pull off the first portion 22 of the release sheet 16 from the second portion 24 in the direction of an arrow A. Generally, such a pressure-sensitive adhesive tape package 10 is mostly opened from the edge. Accordingly, if the package 10 is started to open from the corner as shown in FIG. 5(a), the force concentrates on the corner 46 of the traverse sealed portion 40 and the longitudinal sealed portion 38, and breakage of the sealed portions 38 and 40 is easily started. Once the breakage in the sealed portions 38 and 40 is started, breakage propagates to other portions from the breakage start point as a starting point without additionally applying a large force to break the entire sealed portions 38, 40, and 42. Finally, the pressure-sensitive adhesive tape package 10 reaches the state in FIG. 5(b). As described above, the first portion 26 of the adhesive tape 14 is primarily held on the side of the second portion 24 of the release sheet 16 by existence of the temporary attach portions 50, 52, and 54. As a result, the adhesive agent layer 12 in the first portion 26 of the adhesive tape 14 is exposed.

FIGS. 6(a) to 6(d) show aspects in the case where the adhesive tape of the present invention is used particularly as the patch preparation for medical care or cosmetics, while the adhesive tape of the present invention can also be applied by the same method in the case of use in other application. First, the opened pressure-sensitive adhesive tape package 10 is held by one hand, and placed in the portion for application or in the vicinity of the portion for application as shown in FIGS. 6(a) and 6(b). Next, as shown in FIG. 6(c), while the first portion 22 of the release sheet 16 is held, the release sheet 16 is pulled along the skin in the longitudinal direction thereof and a direction away from the adhesive tape 14. As the release sheet 16 is pulled away, the second portion 28 of the adhesive tape 14 is released from the release sheet 16 and simultaneously applied to the portion for application. Particularly, because the adhesive tape 14 is applied while the release sheet 16 is pulled, the adhesive tape 14 can be applied without a wrinkle. FIG. 6(d) shows the state where the whole adhesive tape 14 is applied to the portion for application to finish application.

The adhesive tape of the present invention can be held by hand because the first portion 22 of the release sheet 16 released off from the adhesive agent layer 12 can be supported by the thumb of the hand on which the adhesive tape is placed. Accordingly, a risk of dropping the adhesive tape when the adhesive tape is applied to the portion for application is small, and worries about shifting of the adhesive tape or hanging of the adhesive tape by gravity in an unintended direction during application are small; for this reason, the adhesive tape can be applied to the portion for application to be targeted for in a carefree manner. The adhesive tape can be easily applied by a single hand even if the portion for application is a back or the like in which application is difficult by oneself.

If in production of such a pressure-sensitive adhesive tape package 10, the adhesive tape 14 and the release sheet 16 cut into predetermined sizes are prepared, and the package is produced one by one in the manner shown in FIG. 2, production efficiency is low and the so-called mass production is extremely difficult. Then, the present invention provides the method for producing a pressure-sensitive adhesive tape package and the facility that improve production efficiency and are suitable for mass production.

Figure 7:
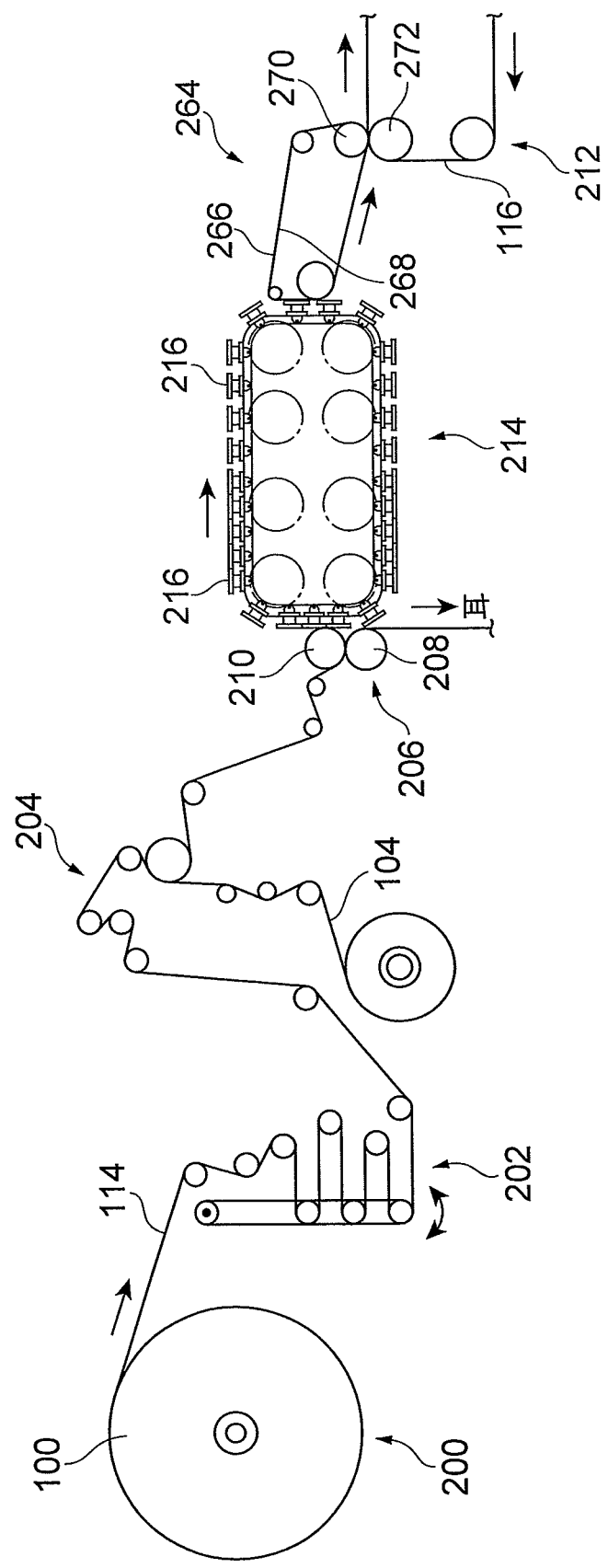
FIG. 7 is a schematic view showing the steps of the method for producing a pressure-sensitive adhesive tape package according to the present invention.
Figure 8:
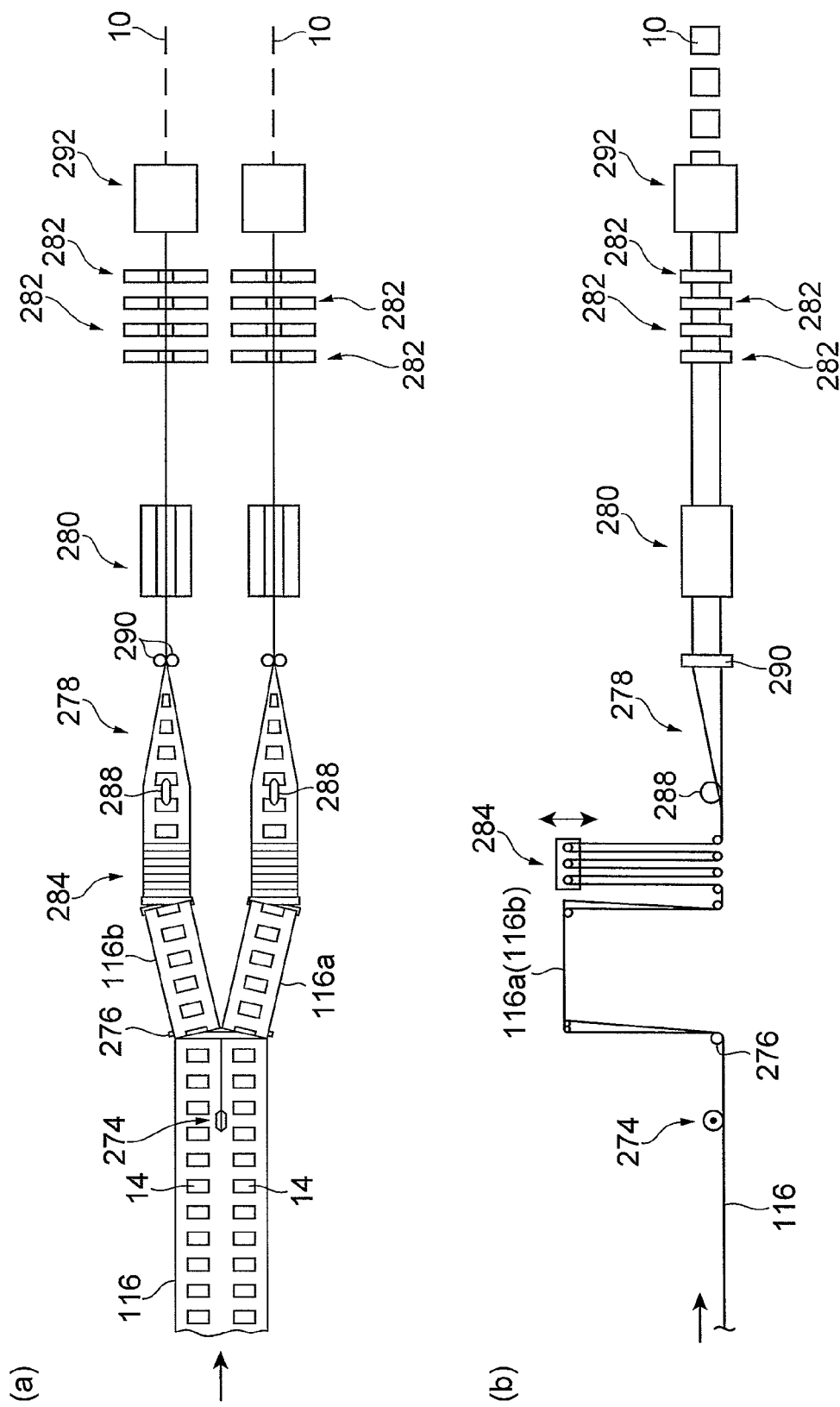
FIG. 8 is a schematic view of the production steps continuing from FIG. 7.

FIG. 7 and FIG. 8 schematically show the method for producing the pressure-sensitive adhesive tape package 10 according to the present invention. In FIG. 7, symbol 200 indicates an adhesive tape web feeding apparatus which holds an adhesive tape roll 100. An adhesive tape web 114 is fed out from the adhesive tape web feeding apparatus 200. The adhesive tape roll 100 is prepared by rolling a long adhesive tape base material, that is, the adhesive tape web 114 into a roll-like shape. The adhesive tape web 114 can be cut vertically and horizontally to form the adhesive tape 14 having a size of product. The adhesive tape web 114 including a portion formed of the support 18 and the adhesive agent layer 12 of the adhesive tape 14 and a liner 104 separably bonded to the adhesive agent layer 12 is suitably used.

The adhesive tape web 114 fed out from the adhesive tape web feeding apparatus 200 is fed via a tension adjusting apparatus 202 to a liner releasing apparatus 204. The liner releasing apparatus 204 is known. The liner 104 is released from the adhesive tape web 114 fed to the liner releasing apparatus 204. In the embodiment, the adhesive tape web 114 without a liner is derived from the liner releasing apparatus 204 with the adhesive agent layer 12 being on the lower side.

As the adhesive tape web 114, those not having the liner 104 or those formed of only a portion serving as the support 18 are thought. For the adhesive tape web 114 not having the liner 104, the liner releasing apparatus 204 is of course unnecessary. For the adhesive tape web 114 formed of only a portion serving as the support 18, a spreading apparatus (not shown) is provided downstream of the adhesive tape web feeding apparatus 200. In the spreading apparatus, an adhesive agent is spread over one surface of the web fed out from the adhesive tape roll, which serves as the support. The spreading apparatus is also known in the related art.

A cutting apparatus 206 for cutting the adhesive tape web 114 in the feeding direction and the traverse direction (horizontal direction intersecting perpendicular to the feeding direction of the adhesive tape web 114) is provided downstream of the liner releasing apparatus 204. Various types of the cutting apparatus 206 are thought. In the embodiment illustrated, a rotary cutter including a die cut roll 208 having a blade and an anvil roll 210 that contacts the die cut roll and rotates is used. When the adhesive tape web 114 is fed between the die cut roll 208 and the anvil roll 210, the adhesive tape 14 having a size of product is punched out of the adhesive tape web 114, and is fed downstream.

Figure 9:
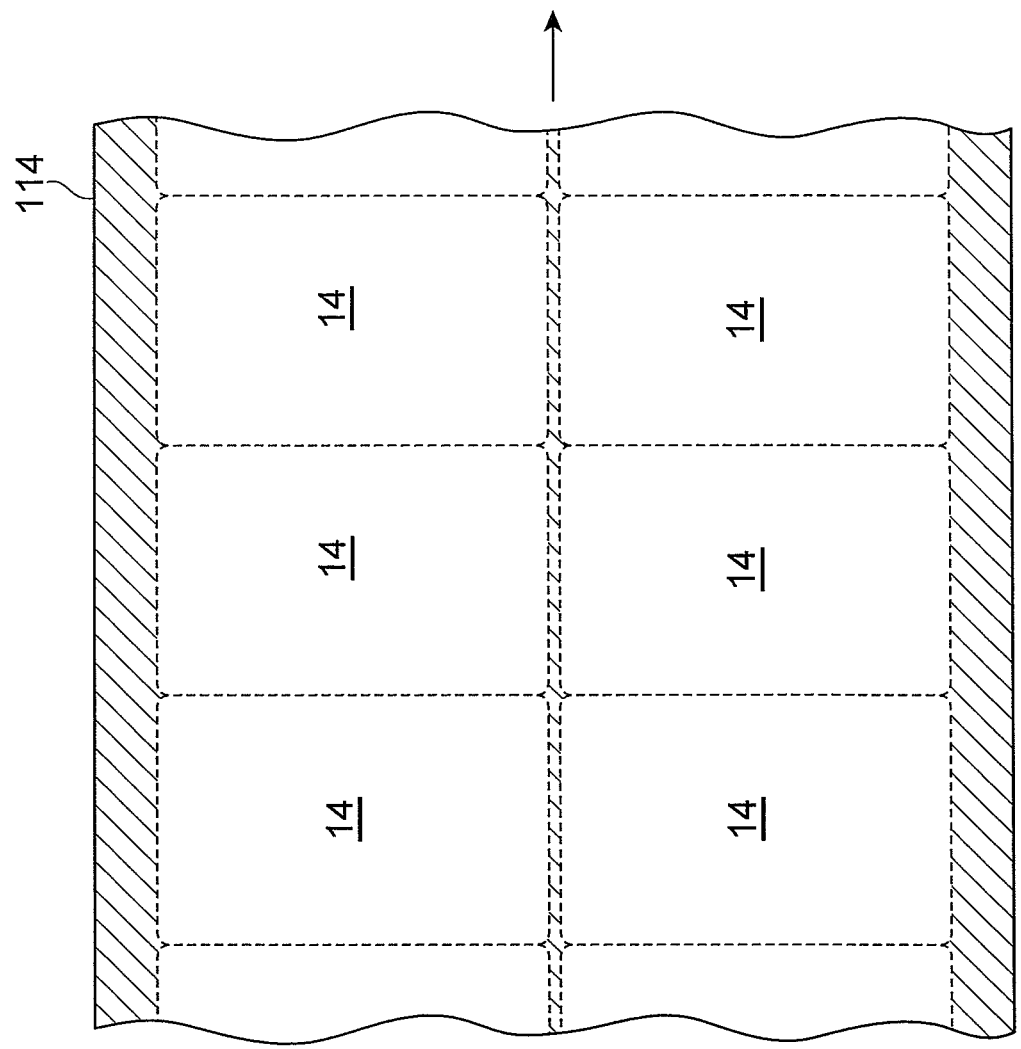
FIG. 9 is a diagram illustrating cutting positions of an adhesive tape web.

In FIG. 9, portions in which the adhesive tape web 114 is punched out are expressed by dotted lines, and hatched portions are discharged as a waste. As understood from FIG. 9, in the present embodiment, the adhesive tape 14 after cutting is fed in two rows in the feeding direction of the adhesive tape web 114 (arrow direction in FIG. 9) from the cutting apparatus 206.

In the cutting apparatus 206 in the present embodiment, the die cut roll 208 is provided on the lower side and the anvil roll 210 is provided on the upper side. Accordingly, the adhesive agent layer of the adhesive tape web 114 contacts the die cut roll 208. For this reason, the surface of the die cut roll 208 is subjected to a known releasing treatment such that the adhesive tape 14 after punching can be easily released from the die cut roll 208, and the tackiness between the die cut roll 208 and the adhesive tape web 114 is made extremely small. The anvil roll 210 is formed of a cylindrical body on which many small holes are formed. The anvil roll 210 has a structure that enables adsorption of the adhesive tape web 114 contacting the surface by sucking air inside of the anvil roll. Accordingly, the punched adhesive tape 14 can be released from the die cut roll 208 without fail. With rotation of the anvil roll 210, the adhesive tape 14 adsorbed by the anvil roll 210 is upwardly guided out of a feeding portion of the cutting apparatus 206 that does not adsorb the adhesive tape.

Individual adhesive tapes 14 fed from the cutting apparatus 206 are fed to the feed position indicated by symbol 212 in FIG. 7, and are bonded to the long release sheet base material, that is, the release sheet web 116 which serves as the release sheet 16. However, the interval between the adjacent adhesive tapes 14 is extremely narrow immediately after punching by the cutting apparatus 206. If the adhesive tapes are placed on the release sheet web 116 as they are, there is no room for heat sealing of the package 10 in the final production step.

Then, in the present embodiment, a separating and conveying apparatus 214 is provided between the cutting apparatus 206 and the feed position 212 to convey the adhesive tapes 14 adjacent to each other in anterior, posterior, left, and right directions while the adjacent adhesive tapes are being separated from each other (interval being increased) in the feeding direction and in the traverse direction (horizontal direction intersecting perpendicular to the feeding direction).

The separating and conveying apparatus conveys the adhesive tapes while increasing the interval between the adjacent adhesive tapes 14 as described above. Various separating and conveying apparatuses are thought, for example, apparatuses including a plurality of robot apparatuses that move individual adhesive tapes 14 to desired positions with a suction type robot arm, or apparatuses including a belt conveyor apparatus.

In the separating and conveying apparatus including a robot apparatus, the arm of the robot apparatus mainly moves in the horizontal direction. For example, when two or more rows of adhesive tapes 14 are fed, it is thought that the layout of arrangement of the apparatuses is large in order to prevent interference between the robot arms.

Figure 10:
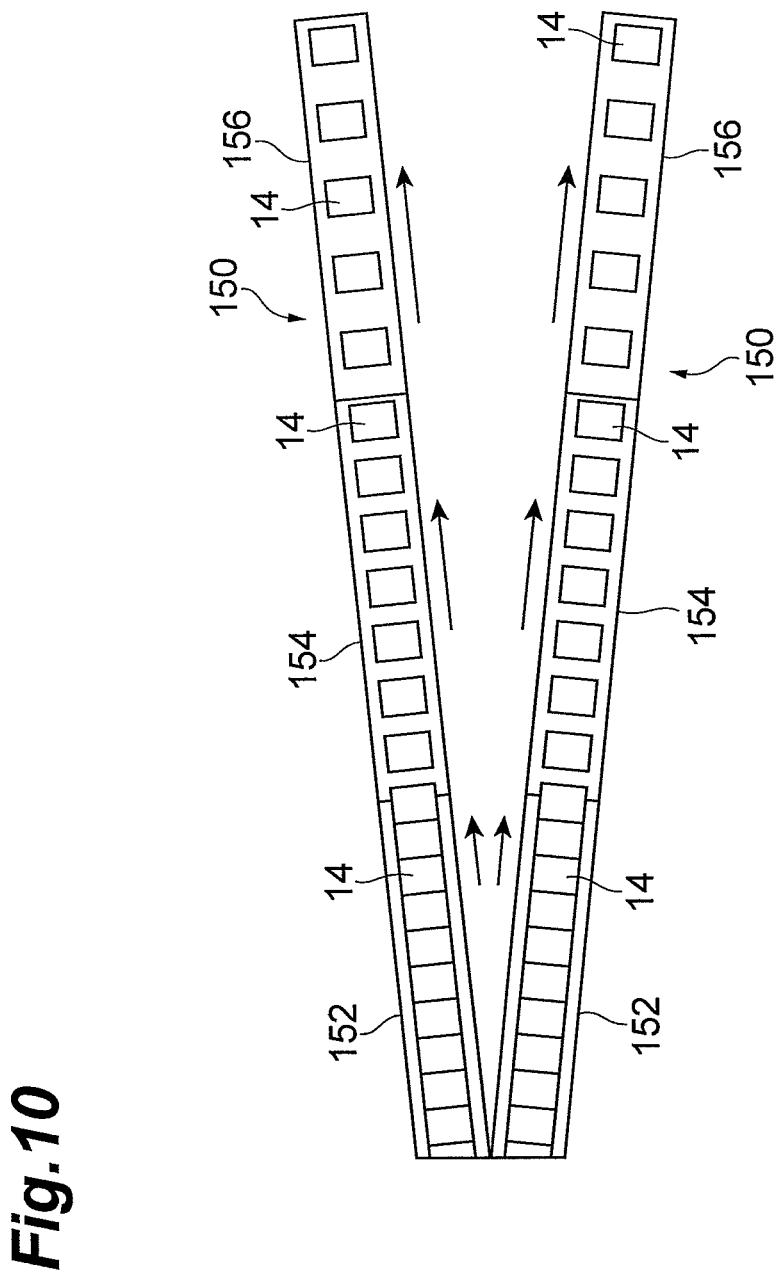
FIG. 10 is a plan view schematically showing an example of separating and conveying apparatus usable for the method for producing a pressure-sensitive adhesive tape package according to the present invention.

As the separating and conveying apparatus including a belt conveyor apparatus, as shown in FIG. 10, a plurality of belt conveyor apparatuses 150 disposed so as to radially extend is thought. Each of the belt conveyor apparatuses 150 includes a plurality of belt conveyors 152, 154, and 156 linearly disposed. The conveying rates of the belt conveyors 152, 154, and 156 become higher as the adhesive tape is conveyed toward the side downstream of each of the belt conveyor apparatuses 150. In such a configuration, the interval in the feeding direction can be increased while the interval between the traverse directions is increased. In the separating and conveying apparatus including the belt conveyors, it is thought that an auxiliary apparatus is complex when feeding of the adhesive tape 14 to the conveyor, passing of the adhesive tape from conveyor to conveyor, and the like are stably operated.

Figure 11:
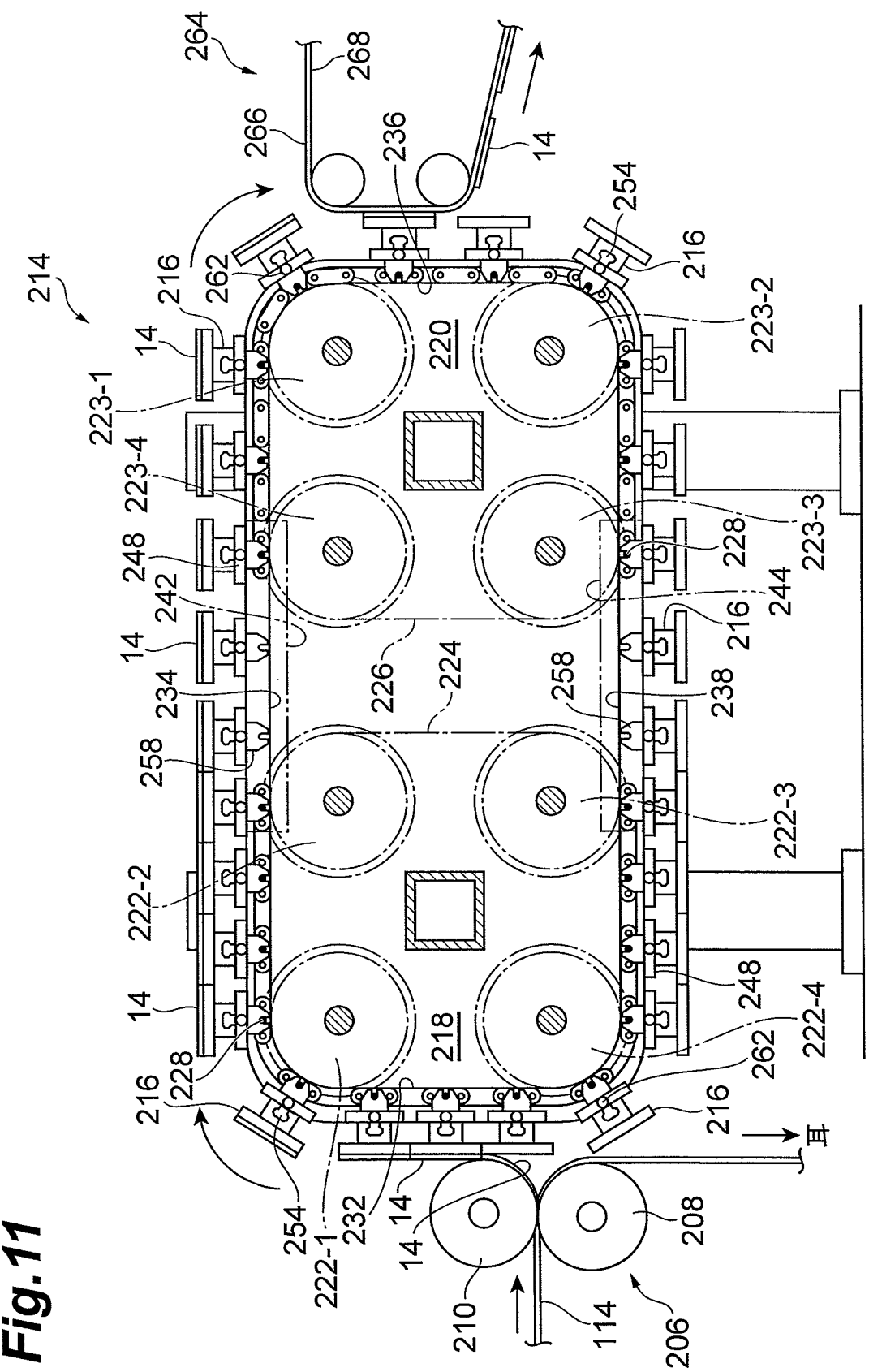
FIG. 11 is a side view schematically showing a suitable separating and conveying apparatus usable for the method for producing a pressure-sensitive adhesive tape package according to the present invention.

FIG. 11 shows a suitable separating and conveying apparatus 214, which is configured to circulate a holding base 216 that contacts and holds the surface of the support 18 of the adhesive tape 14 (surface opposite to the surface including the adhesive agent layer 12), and gradually expands the interval between adjacent holding bases 216 in the anteroposterior direction during movement of the holding bases 216 and at the same time expands the left and right intervals between the holding bases 216. The separating and conveying apparatus has a compact configuration having high efficiency in separating and conveying.

More specifically, the separating and conveying apparatus 214 includes a first circulating chain unit 218 disposed upstream of a production line (side close to the cutting apparatus 206) and a second circulating chain unit 220 disposed downstream of the production line (side away from the cutting apparatus 206). The circulation paths of chains 224 and 226 each include upstream and downstream vertical paths and upper and lower horizontal paths. A pin 228 is disposed at a constant pitch on the outer surfaces of left and right link plates that form the chains 224 and 226. For example, although not limited to, the pitch of the pin 228 in the first circulating chain unit 218 is 100 mm, and the pitch of the pin 228 in the second circulating chain unit 220 is 130 mm.

A guiding plate for guiding the holding base 216 is disposed between left and right sprocket wheels 222 and 223.

The guiding plate defines the circulation path formed of arc paths along the outer shapes of the sprocket wheels 222 and 223 and linear paths. The circulation path consists of a vertically ascending path 232 adjacent to the cutting apparatus 206, an arc path along the outer shape of a sprocket wheel 222-1, an upper traveling path 234 horizontally extending in the flow direction of the production line, an arc path along the outer shape of a sprocket wheel 223-1, a vertically descending path 236 extending downward, an arc path along the outer shape of a sprocket wheel 223-2, a lower traveling path 238 horizontally extending in a direction opposite to the flow direction of the production line, and an arc path along the outer shape of a sprocket wheel 222-4 leading to the vertically ascending path 232, which paths connect to one another.

In the guiding plate, two guiding grooves for guiding the holding base 216 in left and right directions are formed. In the present embodiment, in the upper traveling path 234, the interval between the two guiding grooves is gradually increased as the two guiding grooves are spaced from the cutting apparatus 206. In the lower traveling path 238, the interval between the two guiding grooves is gradually decreased as the two guiding grooves approach to the cutting apparatus 206. In the vertically ascending path 232 and the vertically descending path 236, the respective intervals between the guiding grooves are substantially constant.

Feeding rods 242 and 244 are disposed along the upper traveling path 234 and the lower traveling path 238, respectively, in the left and right sides of the guiding plate. In the feeding rods 242 and 244, a spiral feeding groove is formed. The pitch of the feeding groove is gradually increased along the flow direction of the production line. The pitch of the feeding groove on the side of the first circulating chain unit 218 is substantially equal to the pitch of the pin 228 in the circulating chain unit 218, and that on the side of the second circulating chain unit 220 is substantially equal to the pitch of the pin 228 in the circulating chain unit 220.

The holding base 216 for holding the adhesive tape 14 is held slidably in the left and right traverse directions by a support block 248. In the present embodiment, two holding bases 216 are held on one support block 248. One guiding rod extends from the holding base 216, and enables the holding base 216 to slide left and right along a rail 254 on the support block 248. The tip of the guiding rod is slidably fitted into the corresponding guiding groove in the state where the support block 248 is disposed on the guiding plate.

An inverted U-shaped bracket 258 is fixed to the lower surfaces of both ends of the support block 248. A groove is formed in legs of the bracket 258. The pins 228 on the chains 224 and 226 of the circulating chain units 218 and 220 are fitted into the groove. Accordingly, when the circulating chain units 218 and 220 are driven to circulate the chains 224 and 226, the support block 248 moves with the chains accompanied by the circulation.

Furthermore, a roller bearing 262 is provided on left and right end surfaces of the support block 248. The roller bearing 262 is fitted into the feeding grooves of the feeding rods 242 and 244 in the state where the support block 248 is disposed on the upper traveling path 234 or the lower traveling path 238 of the guiding plate. When the feeding rods 242 and 244 are rotated in the state where the roller bearing 262 is fitted into the feeding grooves of the feeding rods 242 and 244, the support block 248 moves according to the rotational direction to the flow direction of the production line or the opposite direction thereto.

In such a configuration, many support blocks 248 are disposed on the guiding plate as shown in FIG. 11. In the vertically ascending path 232 of the guiding plate, the pitch of the pin 228 in the first circulating chain unit 218 is narrow, and the interval between adjacent support blocks 248 in the anteroposterior direction in the circulating direction is narrow. The holding base 216 held there is in contact with or is extremely little spaced from its adjacent holding base 216 in the circulating direction. In the vertically descending path 236 of the guiding plate, the interval between the guiding grooves is largest, and adjacent holding bases 216 in left and right are largely spaced from each other.

In this state, the separating and conveying apparatus 214 is started. Then, the support block 248 located in the vertically ascending path 232 of the guiding plate ascends with movement of the pin 228 disposed in the chain 224 of the first circulating chain unit 218, and travels the upper traveling path 234 of the guiding plate. Then, the pin 228 of the first circulating chain unit 218 fitted into the groove of the bracket 258 in the support block 248 starts descending, and is detached from the bracket 258. At this timing, the roller bearings 262 disposed on the left and right ends of the support block 248 are inserted into the feeding grooves of the upper feeding rod 242.

The feeding rod 242 is rotationally driven in a predetermined direction. Thereby, the support block 248 moves in the upper traveling path 234 in the flow direction of the production line. At this time, because the pitch of the feeding groove is gradually increased, the traveling speed of the support block 248 also increases and the interval between adjacent support blocks 248 in the anteroposterior direction increases. Since the interval between the two guiding grooves of the guiding plate is also gradually increased, two holding bases 216 move on the support block 248 in a direction in which the two holding bases are spaced from each other.

When the support block 248 reaches the tip of the feeding rod 242 (end on the side away from the cutting apparatus 206), the roller bearing 262 of the support block 248 comes out from the feeding groove. At this time, the pin 228 in the chain 226 of the second circulating chain unit 220 is already fitted into the groove of the bracket 258 of the support block 248, and the support block 248 is moved to the right and downwardly in FIG. 11 by the drive force of the second circulating chain unit 220.

The operation of the support block 248 when traveling from the vertically descending path 236 via the lower traveling path 238 to the vertically ascending path 232 is the same as that when traveling from the vertically ascending path 232 via the upper traveling path 234 to the vertically descending path 236. Accordingly, the description of the details thereof will be omitted, but it is easily understood that the intervals anterior and posterior to the support block 248 are narrowed in the lower traveling path 238 and the interval between the two holding bases 216 on the support block 248 is also narrowed.

The support block 248 is moved by the upper and lower feeding rods 242 and 244 of the first and second circulating chain units 218 and 220. The timing to change from the circulating chain units 218 and 220 to the feeding rods 242 and 244 and the timing to convey from the feeding rods 242 and 244 to the circulating chain units 220 and 218 can be controlled by driving the first and second circulating chain units 218 and 220 and the upper and lower feeding rods 242 and 244 by a suitable transmission system, thereby separating and conveying the adhesive tape 14 with high precision.

The separating and conveying apparatus 214 is disposed adjacent to the cutting apparatus 206. More specifically, in the state where the support block 248 is located in the lowest portion of the vertically ascending path 232 of the separating and conveying apparatus 214, the separating and conveying apparatus 214 is disposed such that the surface of the holding base 216 on the support block 248 is in contact with the outer surface of the anvil roll 210 of the cutting apparatus 206. Thereby, the adhesive tape 14 punched out from the adhesive tape web 114, held on the anvil roll 210, and fed out is sequentially transferred onto the holding base 216.

The anvil roll 210 vacuum adsorbs the adhesive tape 14 during a period from introduction of the adhesive tape 14 to transfer of the adhesive tape 14 onto the holding base 216. Except this period, the anvil roll 210 air blows to facilitate transfer of the adhesive tape 14 onto the holding base 216. In the present embodiment, many small holes are formed on the surface of the holding base 216 to generate a vacuum adsorption force. Various means for giving a vacuum adsorption force to the holding base 216 can be thought. Although not shown, for example, a vacuum port is formed on at least one end of the support block 248. The vacuum port is brought into contact with a vacuum suction nozzle provided along the guiding plate 230 when the support block 248 is located in the vertically ascending path 232. The vacuum port communicates with the inner space of the holding base 216 with a tube or the like. Thereby, a vacuum adsorption force generates only when the support block 248 is located on the vertically ascending path 232, which enables the support block 248 to receive the adhesive tape 14 from the anvil roll 210 of the cutting apparatus 206.

When the adhesive tape 14 is on the anvil roll 210, the adhesive agent layer 12 is exposed, and the adhesive agent layer 12 contacts the holding base 216. Accordingly, the surface of the holding base 216 is suitably subjected to a proper surface treatment in order to easily remove the adhesive tape 14 from the holding base 216 when the adhesive tape 14 is sent to the subsequent step.

Figure 12:
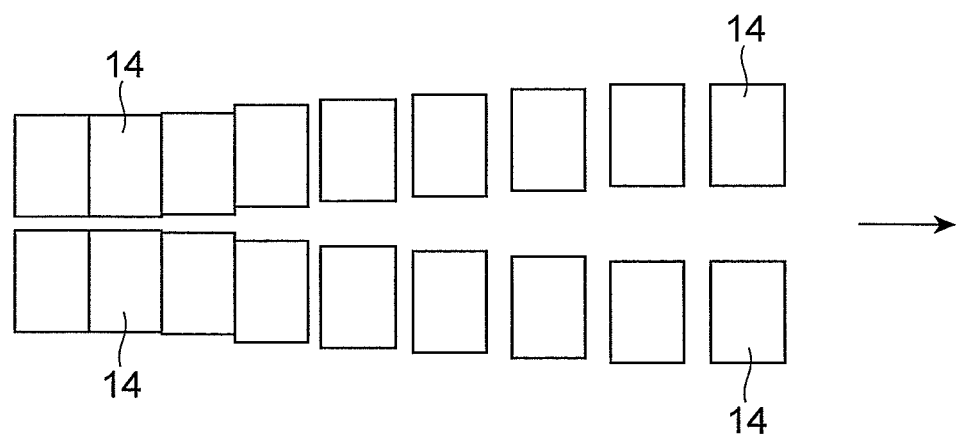
FIG. 12 is a schematic diagram showing the trajectory of the adhesive tape conveyed by the separating and conveying apparatus in FIG. 11.

Once the adhesive tapes 14 are placed on the holding bases 216, the intervals between the adhesive tapes adjacent to each other in anterior, posterior, left, and right directions are increased in the upper traveling path 234 as understood from the operation of the separating and conveying apparatus 214 described above. The adhesive tapes 14 are fed as they are to a bonding apparatus 264 for bonding the adhesive tape 14 to the release sheet web 116. FIG. 12 shows the state where the adhesive tapes 14 are conveyed in the upper traveling path 234.

The bonding apparatus 264 has a vacuum adsorbing belt conveyor 266. A belt 268 of the belt conveyor 266 is disposed so as to partially contact the surface of the holding base 216 located in the vertically descending portion 236 of the separating and conveying apparatus 214. Accordingly, the belt 268 contacts the support 18 of the adhesive tape 14 held on the holding base 216. Because the belt conveyor 266 is of a vacuum adsorption type, the adhesive tape 14 contacting the belt 268 is transferred from the holding base 216 to the belt 268. At this time, the intervals between the adhesive tapes 14 adjacent to each other in anterior, posterior, left, and right directions are kept also on the belt 268, and the adhesive agent layer 12 of the adhesive tape 14 is exposed downwardly.

The bonding apparatus 264 has a press roller 272 contacting a roller indicated by symbol 270 of the belt conveyor 266. Between the press roller 272 and the roller 270, the release sheet web 116 serving as the release sheet 16 is fed. Accordingly, the adhesive tape 14 fed between the press roller 272 and the roller 270 (feed position) is bonded to the upper surface of the release sheet web 116, and is further conveyed downstream in this state with the release sheet web 116.

The release sheet web 116, although not shown, is held by a release sheet web feeding apparatus in a roll-like state, and is fed out from the apparatus. The surface of the release sheet web 116 to which the adhesive tape 14 is bonded is suitably subjected to a release treatment in advance.

The release sheet web 116 to which the adhesive tape 14 is bonded is then slit on the longitudinal center line in the slitter 274 as shown in (a) of FIG. 8. In each of two release sheet webs 116a and 116b obtained by slitting, a row of adhesive tapes 14 is aligned, and predetermined spaces are formed between adjacent adhesive tapes 14 in the anteroposterior direction.

Thereafter, in a portion indicated by symbol 276, the two release sheet webs 116a and 116b slit are pulled in opposite directions to form a predetermined interval between the two release sheet webs 116a and 116b. The interval is formed in consideration of the installation space or the like of a bending apparatus 278, a heat sealing apparatus 280, and a temporary attaching apparatus 282 in the post stages. Namely, the interval between the two release sheet webs 116a and 116b is properly determined according to the installation positions and types of these apparatuses in the post stages. In some cases, it is thought that an increase of the interval is unnecessary.

The slit release sheet webs 116a and 116b each are continuously fed to the bending apparatus 278 via the buffer apparatus 284. In the present embodiment, sealing is of a box motion type using heat sealing performed by the heat sealing apparatus 280 and a temporary attaching sealer operating mechanism using the temporary attaching apparatus 282.

Figure 13:
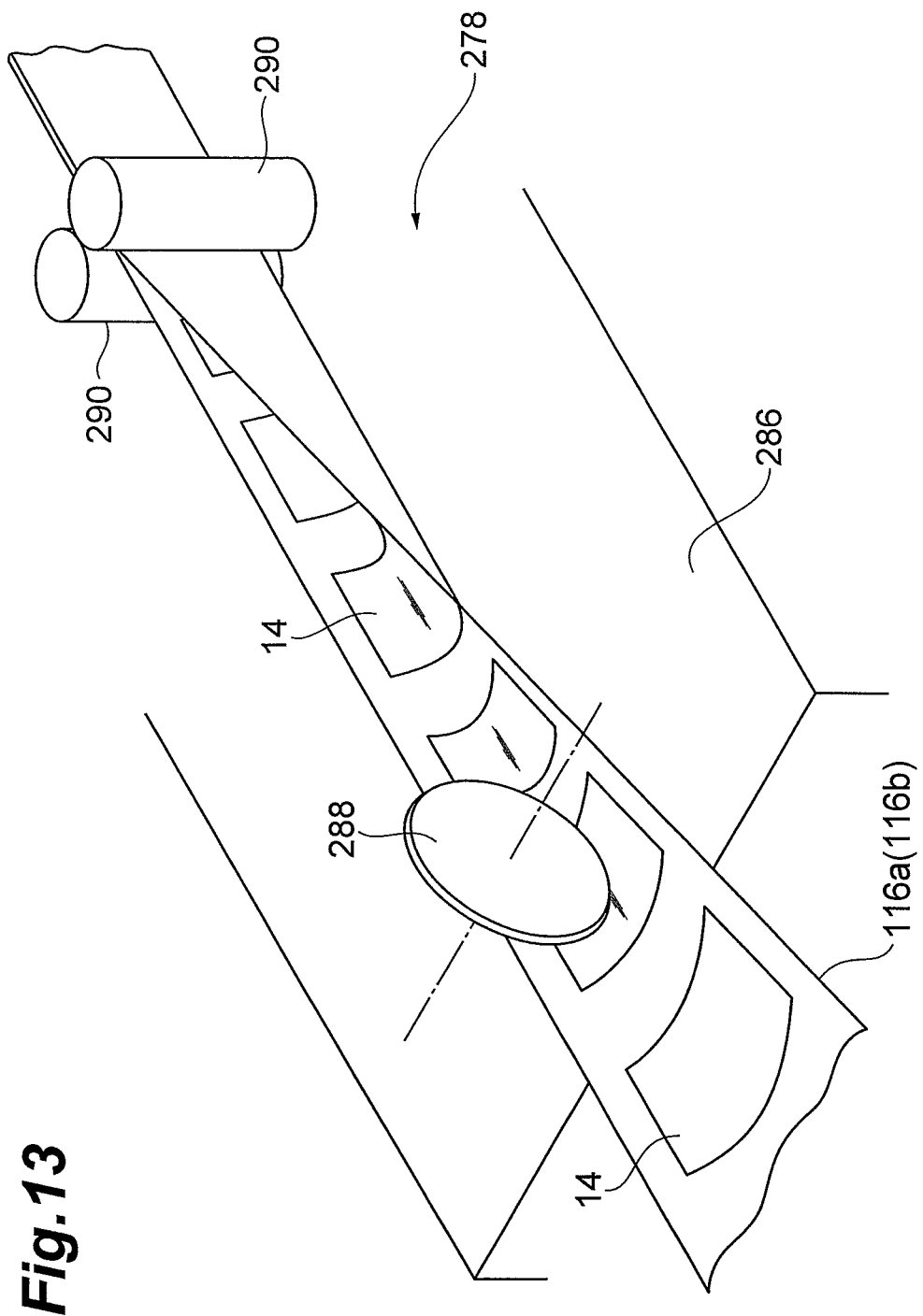
FIG. 13 is a perspective view schematically showing a bending apparatus usable for the method for producing a pressure-sensitive adhesive tape package according to the present invention.

As shown in FIG. 13, the bending apparatus 278 includes a base 286 having a smooth surface on which the release sheet web 116a or 116b is placed; a disk presser roller 288 contacting the surface of the base 286, having a horizontal rotational axis, and disposed in the feeding direction of the release sheet web 116a or 116b; and a pair of press rollers 290 disposed downstream of the presser roller 288, having a vertical rotational axis, and disposed intersecting perpendicular to the feeding direction of the release sheet web 116a or 116b. The press rollers 290 contact each other and rotate. The presser roller 288 contacts a portion corresponding to substantially the longitudinal center line of the release sheet web 116a or 116b conveyed on the base 286. The presser roller 288 assists the release sheet web 116a or 116b and the adhesive tape 14 bonded thereto to be folded in two at the contacting point. The release sheet web 116a or 116b and the adhesive tape 14 bonded thereto are completely folded in two by the press roller 290.

In the bending apparatus 278, a method for raising both sides of the release sheet web 116a or 116b is employed. By raising both sides thereof, the rotational amount of each side of the release sheet web 116a or 116b is only 90°, and the amount of deviation can be reduced.

The position in which the presser roller 288 contacts the release sheet web 116a or 116b is not on the longitudinal center line of the release sheet web 116a or 116b, but is suitably a position slightly shifted from the longitudinal center line. Thereby, the edge 20 of the first portion 22 and the edge 20 of the second portion 24 of the release sheet 16 in the final product pressure-sensitive adhesive tape package 10 are slightly deviated from each other as shown in FIG. 1. The deviated portion of the edge 20 provides an effect of easily holding the release sheet 16 with fingers to easily separate the first portion 22 from the second portion 24.

The release sheet webs 116a and 116b folded in two by the bending apparatus 278 are fed to the heat sealing apparatus 280. The heat sealing apparatus 280 having a known configuration can be used. Although the details are not shown in the diagram, in the present embodiment, a box motion type heat sealing apparatus including a pair of heating heads that can contact each other and be spaced from each other is used. As known, a projection is formed in a portion of the heating head corresponding to the position contacting the release sheet web 116a or 116b to heat seal the web. In the present embodiment, the heating head is configured so as to heat seal the portion corresponding to four final products.

Figure 14:
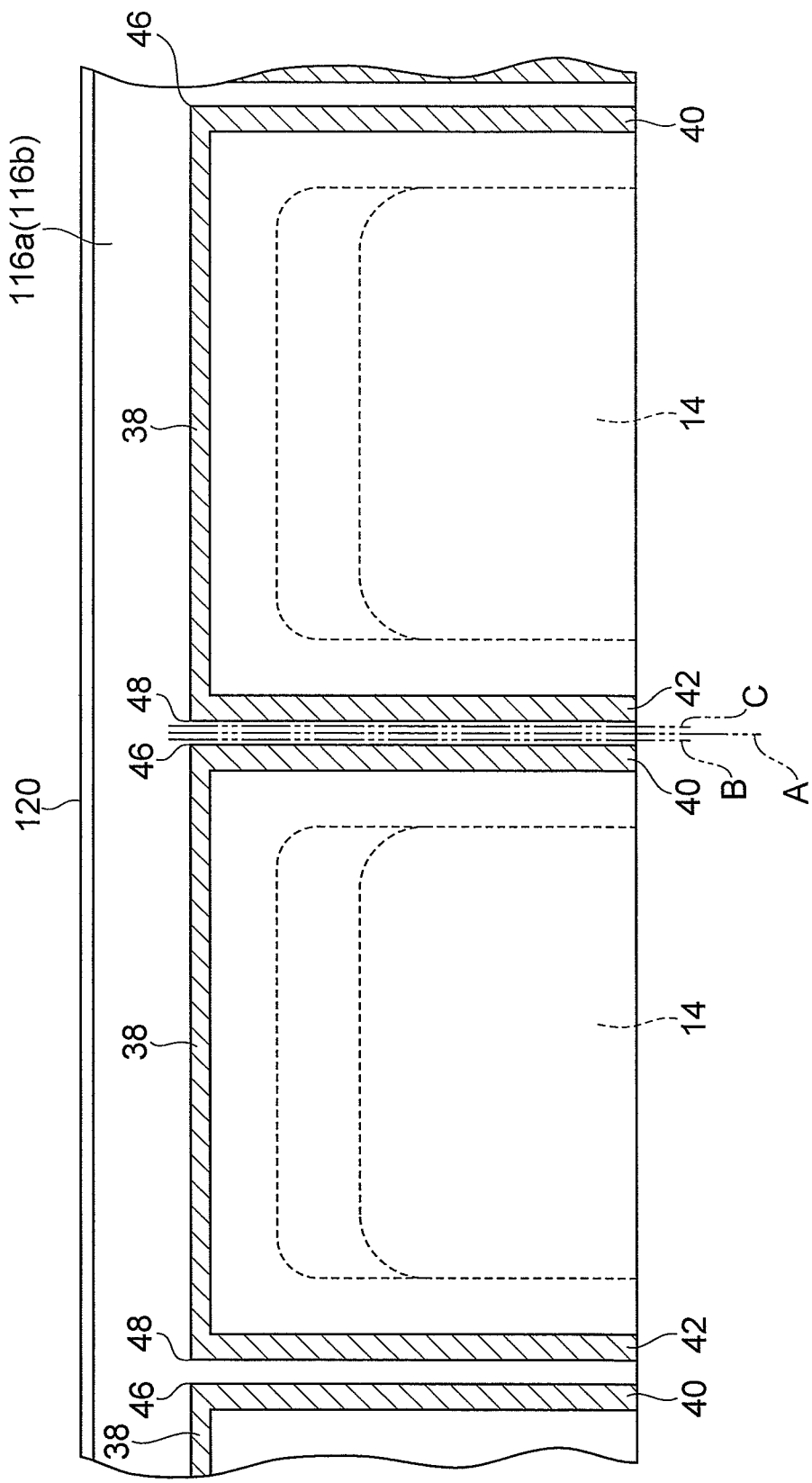
FIG. 14 is a front view of a release sheet web in which the positions of sealed portions are shown.

In the present embodiment, the hatched portions in FIG. 14 are heat sealed. The space surrounded by three sealed portions 38, 40, and 42 and the bent portions of the release sheet web 116a or 116b defines the accommodating space for the adhesive tape 14. It is noted that in the present embodiment, two sealed portions are formed between adjacent adhesive tapes 14 as indicated by symbols 40 and 42. Of course, the sealed portions 40 and 42 can be integrated into one. However, when two heat-sealed portions are formed between adjacent adhesive tapes 14 as shown in FIG. 14, the widths of the sealed portions 40 and 42 in the final products can be kept constant even if the cutting position is slightly deviated. Namely, even if the cutting position is changed as shown with long dashed double-short dashed lines indicated by symbols A, B, and C in FIG. 14, this does not affect the widths of the sealed portions 40 and 42. Thus, if the widths of the sealed portions 40 and 42 are constant, an effect of allowing a constant force applied to the sealed portions 40 and 42 during opening of the package can be attained.

The sealed portion 38 formed parallel to the longitudinal direction of the release sheet web 116a or 116b is largely spaced from a free edge 120 of the release sheet web 116a or 116b in the longitudinal direction. Thereby, in the final product pressure-sensitive adhesive tape package 10, the outer portion from the sealed portion 38 functions as a holding portion 44. The holding portion is easy to hold with fingers, and opening the package is easy. As described above, the edges 20 of the first portion 22 and the second portion 24 in the release sheet 16 are slightly displaced to facilitate separation of the layered portion of the release sheet 16 that forms the holding portion 44, and the package is easier to open.

The sealed portions 38, 40, and 42 are linear, and approximately right-angled corners 46 and 48 are formed in their cross portions. Furthermore, as described above, the sealed portions 40 and 42 are also slightly spaced from the corresponding edges in the final product 10 as shown in FIG. 1, and therefore the corners 46 and 48 are also spaced from the edges 20, 34, and 36, respectively. The corners 46 and 48 are spaced from the edges 20, 34, and 36 to attain an effect of concentrating a force on this portion and much facilitating opening the package.

As the heat seal, the so-called easy peel techniques is used. The easy peel means easy releasabilty as described in the Patent Map for Technical Fields, General 21 "Adhesion," p. 335, available from the Japan Patent Office website (www.j-po.go.jp/shiryou/s_sonota/map/ippan21/4/4-3-1.htm), and refers to containers and packages sealed by heat sealing to provide easy releasing upon opening. Specifically, examples of easy peel include various types such as a cohesive failure type in which the adhesive layer between the first portion 22 and second portion 24 of the release sheet 16 itself is broken to be released off, an interlayer releasing type in which adhesive strength between the adhesive layer and the first portion 22 or second portion 24 is small, and the first portion 22 or the second portion 24 is released off from the adhesive layer at the time of opening, and an interlayer releasing type using an easy-releasable resin such as EVA, but are not particularly limited thereto; in the case where a sheet material in which a polyethylene layer is disposed on the surface is used as the release sheet 16, those with a two-layered structure composed of a resin layer containing a high density polyethylene as a principal component and an easy peel resin layer prepared by adding a resin causing the cohesive failure to a low density polyethylene, for example, may be used as an easy peel adhesive layer.

In the present embodiment, the heat sealing apparatus 280 is of a box motion type. Namely, the heat sealing apparatus 280 is configured to continuously move the release sheet web 116a or 116b, sandwich the release sheet web 116a or 116b by a pair of heating heads, and feed the release sheet web to the next step when heat seal is completed. However, a continuous heat sealing apparatus including a pair of heat sealing rollers contacting each other and rotating can also be used.

The release sheet web 116a or 116b heat sealed by the heat sealing apparatus 280 is further continuously fed downstream, and fed to the temporary attaching apparatus 282. In the present embodiment, four temporary attaching apparatuses 282 are provided for each of the release sheet webs 116a and 116b, which enable temporary attachment of four adhesive tapes 14 and each of the release sheet webs 116a and 116b at the same time. The temporary attaching apparatus 282 basically has the same configuration as that of a known box motion type heat sealing apparatus, and includes a pair of heating heads that can contact and depart from each other. In the present embodiment, the heating head is configured to form dotted temporary attach portions 50, 52, and 54 as shown in FIG. 1.

In the temporary attaching apparatus 282 having such a configuration, when the release sheet web 116a or 116b continuously flowed is flowed to a predetermined position, the pair of heating heads approach each other in synchronization with the flow rate of the release sheet web to sandwich the release sheet web 116a or 116b. Then, heat is applied to the surface of the release sheet web 116a or 116b for a constant time. Thereby, a thermoplastic material disposed in the innermost layer of the release sheet web 116a or 116b is molten, and adhered to the support 18 of the adhesive tape 14. Thereby, the extending portion 30 of the adhesive tape 14 is temporarily attached to the release sheet web.

The temporary attachment and heat sealing can be performed at the same time by providing a projection for forming a temporary attach portion in the heating head of the heat sealing apparatus 280 above. It can be easily understood that instead of the box motion type temporary attaching apparatus, the temporary attachment can be performed using a continuous temporary attaching apparatus including a pair of heating rollers contacting each other and rotating.

After temporary attachment is performed, the release sheet webs 116a and 116b are cut by a cutting apparatus indicated by symbol 292 in FIG. 8, and the final product pressure-sensitive adhesive tape package 10 shown in FIG. 1 is completed. After that, the pressure-sensitive adhesive tape package 10 is subjected to check of the product, outer packaging, and the like.

As above, the suitable embodiment according to the present invention has been described in detail, and needless to say, the present invention will not be limited to the embodiment above.

For example, in the above embodiment, after the adhesive tape web 114 is cut, two rows of adhesive tapes 14 are fed. Alternatively, a single row of adhesive tapes may be fed. In this case, in the separating and conveying apparatus 214, only one holding base 216 may be provided on the support block 248. The holding base does not move in the left and right traverse directions, and may be configured to increase the interval only anteroposterior to the support block 248. The release sheet web 116 is not slit, and needless to say, the slitter 274 is unnecessary.

It is also thought that the adhesive tape web 114 is cut into three, and three rows of adhesive tapes 14 are fed. In this case, in the separating and conveying apparatus 214, three holding bases 216 are provided for one support block 248, and three guiding grooves are provided to guide the three holding bases 216. When four or more rows of adhesive tapes 14 are fed, the separating and conveying apparatus 214 is similarly modified.

Figure 15:
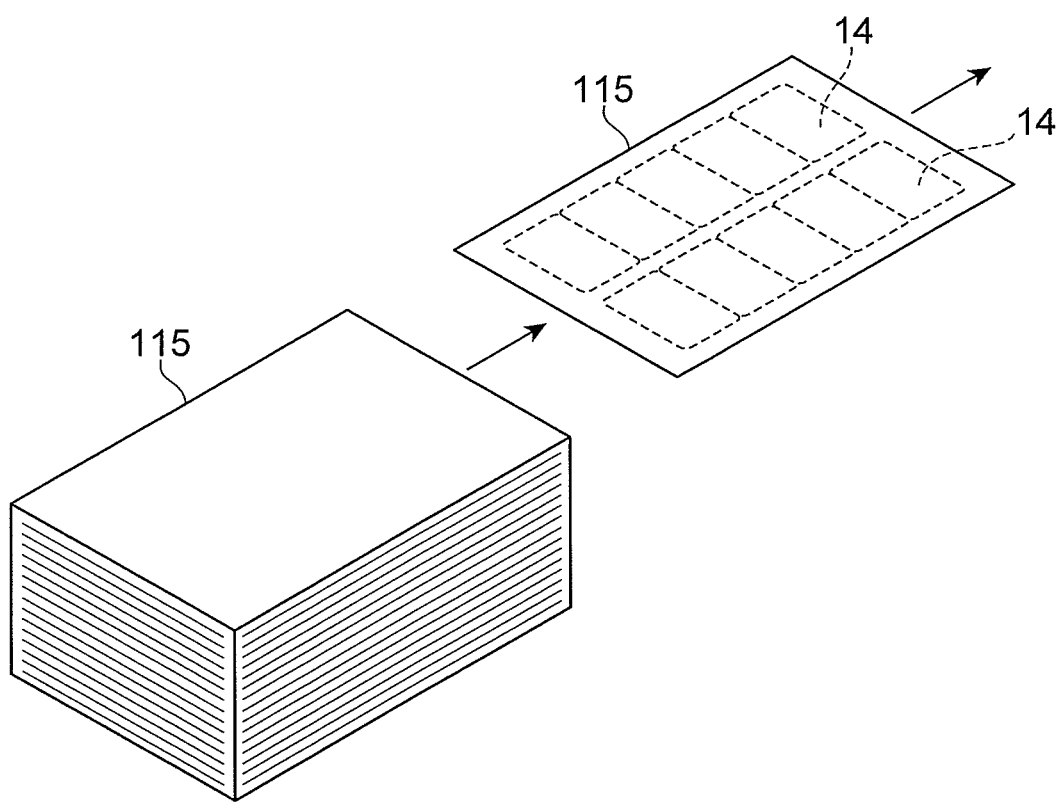
FIG. 15 is a schematic view showing another embodiment of the method for producing a pressure-sensitive adhesive tape package according to the present invention.

The adhesive tape 14 is not limited to an adhesive tape obtained by cutting the adhesive tape web 114 fed out from the roll, and may be an adhesive tape obtained by cutting a short web, or the so-called sheet-fed adhesive tape base material 115 as shown in FIG. 15.

Figure 16:
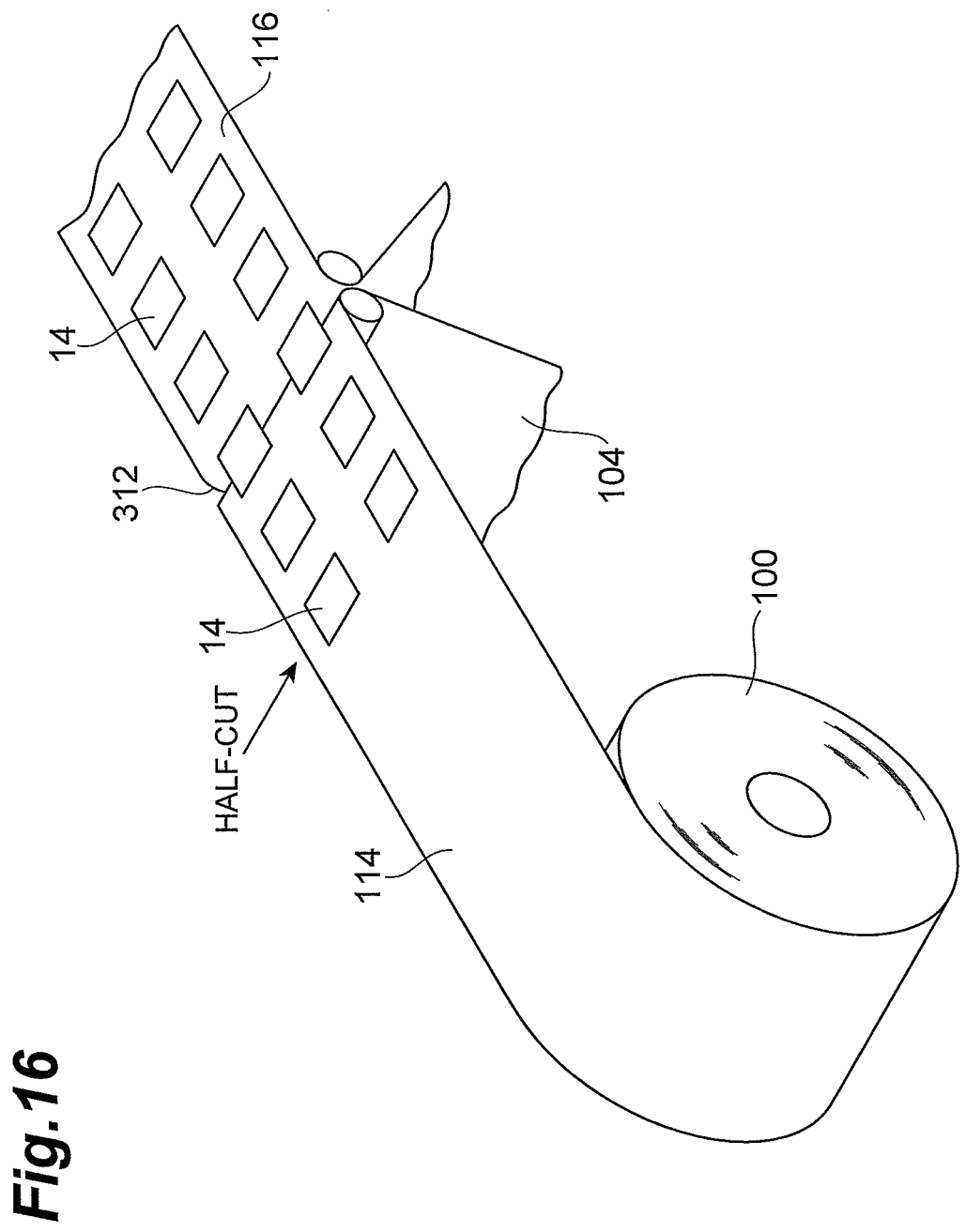
FIG. 16 is a schematic view showing still another embodiment of the method for producing a pressure-sensitive adhesive tape package according to the present invention.

Furthermore, in the above embodiment, after the liner 104 is removed from the adhesive tape web 114 fed from the adhesive tape roll 100, the adhesive tape 14 having a size of the product is cut out. As schematically shown in FIG. 16, a method for half-cutting the adhesive tape web 114 so as to leave the adhesive tape 14, which is the product, on the liner 104 before removal of the liner 104 is also thought. In this case, the adhesive tape 14 can be conveyed by the liner 104. By half-cutting the adhesive tape 14 at a predetermined interval in advance, and feeding the adhesive tape 14 at a predetermined feed position 312 while the liner 104 is being removed, the adhesive tape 14 is sequentially bonded at the feed position 312 at the predetermined interval to the release sheet web 116 flowed at the same speed. Accordingly, in this case, the above separating and conveying apparatus 214 is unnecessary.

When the adhesive tape 14 is half-cut without providing an interval between the adhesive tapes 14, the adhesive tape 14 can also be sequentially bonded to the release sheet web 116 at the predetermined interval by properly setting the feeding rate of the adhesive tape 14 or the timing to feed the adhesive tape to the feed position 312 and the feeding rate of the release sheet web 116 or the timing to feed and stop the release sheet web 116.

REFERENCE SIGNS LIST

10 . . . pressure-sensitive adhesive tape package, 12 . . . adhesive agent layer, 14 . . . pressure-sensitive adhesive tape, 16 . . . release sheet, 18 . . . support, 38, 40, 42 . . . sealed portion, 50, 52, 54 . . . temporary attach portion, 55 . . . means for reducing an adhesive force, 100 . . . adhesive tape roll, 104 . . . liner, 114 . . . adhesive tape web (adhesive tape base material), 115 . . . adhesive tape base material, 116 . . . release sheet web (release sheet base material), 116a, 116b . . . slit release sheet web, 200 . . . adhesive tape web feeding apparatus, 202 . . . tension adjusting apparatus, 204 . . . liner releasing apparatus, 206 . . . cutting apparatus, 208 . . . die cut roll, 210 . . . anvil roll, 212 . . . feed position, 214 . . . separating and conveying apparatus, 216 . . . holding base, 218 . . . first circulating chain unit, 220 . . . second circulating chain unit, 224, 226 . . . chain, 228 . . . pin, 232 . . . vertically ascending path, 234 . . . upper traveling path, 236 . . . vertically descending path, 238 . . . lower traveling path, 242, 244 . . . feeding rod, 248 . . . support block, 254 . . . rail, 258 . . . bracket, 262 . . . roller bearing, 264 . . . bonding apparatus, 266 . . . belt conveyor, 268 . . . belt, 270 . . . roller, 272 . . . press roller, 274 . . . slitter, 278 . . . bending apparatus, 280 . . . heat sealing apparatus, 282 . . . temporary attaching apparatus, 284 . . . buffer apparatus, 286 . . . base, 288 . . . presser roller, 290 . . . press roller, 292 . . . cutting apparatus, 312 . . . feed position

The invention claimed is:

1. A method for producing a pressure-sensitive adhesive tape package, the pressure-sensitive adhesive tape package accommodating a pressure-sensitive adhesive tape having a support and an adhesive agent layer provided on one surface of the support, the pressure-sensitive adhesive tape package comprising a release sheet to which the adhesive agent layer of the adhesive tape is releasably attached, the method comprising:
　a step of feeding a release sheet base material serving as the release sheet to a predetermined feed position;
　a step of sequentially feeding a plurality of adhesive tapes in a row to the release sheet base material at the feed position, and bonding the adhesive tapes to the release sheet base material such that predetermined spaces are formed between the adhesive tapes adjacent in anterior and posterior directions of the feeding direction;
　a step of folding the release sheet base material with the adhesive tape in two;
　a step of sealing a predetermined portion of the release sheet base material to form the two-folded release sheet base material including a plurality of accommodating spaces each of which accommodates one adhesive tape;
　a step of temporarily attaching a part of each adhesive tape to the release sheet base material; and
　a step of cutting the release sheet base material to form the pressure-sensitive adhesive tape package;
　wherein the step of bonding the adhesive tape to the release sheet base material comprises:
　a substep of cutting an adhesive tape base material serving as the adhesive tape to form a row of adhesive tapes; and
　a substep of separating adjacent adhesive tapes from each other, and feeding the adhesive tapes to the feed position while intervals between the adjacent adhesive tapes are increasing.

2. The method for producing a pressure-sensitive adhesive tape package according to claim 1, wherein the sealing is heat sealing.

3. The method for producing a pressure-sensitive adhesive tape package according to claim 2, wherein the temporary attachment is performed by thermal bonding.

4. The method for producing a pressure-sensitive adhesive tape package according to claim 2, wherein in the step of sealing a predetermined portion of the release sheet base material, two sealed portions are formed at a constant interval between adjacent accommodating spaces, and
　in the step of cutting the release sheet base material, cutting is performed between the two sealed portions.

5. The method for producing a pressure-sensitive adhesive tape package according to claim 1, wherein the temporary attachment is performed by thermal bonding.

6. The method for producing a pressure-sensitive adhesive tape package according to claim 1, wherein in the step of sealing a predetermined portion of the release sheet base material, two sealed portions are formed at a constant interval between adjacent accommodating spaces, and
　in the step of cutting the release sheet base material, cutting is performed between the two sealed portions.

7. A method for producing a pressure-sensitive adhesive tape package, the pressure-sensitive adhesive tape package accommodating a pressure-sensitive adhesive tape having a support and an adhesive agent layer provided on one surface of the support, the pressure-sensitive adhesive tape package comprising a release sheet to which the adhesive agent layer of the adhesive tape is releasably attached, the method comprising:
　a step of feeding a release sheet base material serving as the release sheet to a predetermined feed position;
　a step of sequentially feeding a plurality of rows of a plurality of adhesive tapes to the release sheet base material at the feed position, and bonding the adhesive tapes to the release sheet base material such that predetermined spaces are formed between the adhesive tapes adjacent in anterior, posterior, left, and right directions of the feeding direction;

a step of slitting the release sheet base material along a longitudinal direction thereof to form a plurality of release sheet base materials, a row of adhesive tapes being bonded to each of the release sheet base materials;

a step of folding the slit release sheet base material with the adhesive tape in two;

a step of sealing a predetermined portion of the release sheet base material to form the two-folded release sheet base material including a plurality of accommodating spaces each of which accommodates one adhesive tape;

a step of temporarily attaching the release sheet base material to a part of each adhesive tape; and a step of cutting the release sheet base material to form the pressure-sensitive adhesive tape package;

wherein the step of bonding the adhesive tape to the release sheet base material comprises:

a substep of cutting an adhesive tape base material serving as the adhesive tape to form a plurality of rows of adhesive tapes; and a substep of separating the adhesive tapes adjacent in anterior, posterior, left, and right directions from each other and feeding the adhesive tapes to the feed position while intervals between the adjacent adhesive tapes are increasing.

8. The method for producing a pressure-sensitive adhesive tape package according to claim 7, wherein the sealing is heat sealing.

9. The method for producing a pressure-sensitive adhesive tape package according to claim 8, wherein the temporary attachment is performed by thermal bonding.

10. The method for producing a pressure-sensitive adhesive tape package according to claim 8, wherein in the step of sealing a predetermined portion of the release sheet base material, two sealed portions are formed at a constant interval between adjacent accommodating spaces, and in the step of cutting the release sheet base material, cutting is performed between the two sealed portions.

11. The method for producing a pressure-sensitive adhesive tape package according to claim 7, wherein the temporary attachment is performed by thermal bonding.

12. The method for producing a pressure-sensitive adhesive tape package according to claim 7, wherein in the step of sealing a predetermined portion of the release sheet base material, two sealed portions are formed at a constant interval between adjacent accommodating spaces, and in the step of cutting the release sheet base material, cutting is performed between the two sealed portions.

* * * * *